(12) United States Patent
Kondo et al.

(10) Patent No.: US 11,445,932 B2
(45) Date of Patent: Sep. 20, 2022

(54) BIOLOGICAL INFORMATION MEASUREMENT DEVICE AND BIOLOGICAL INFORMATION MEASUREMENT SYSTEM

(71) Applicant: SONY CORPORATION, Tokyo (JP)

(72) Inventors: Yuta Kondo, Kanagawa (JP); Yasuhide Hyodo, Tokyo (JP); Kazunari Yoshifuji, Tokyo (JP); Takanori Ishikawa, Saitama (JP)

(73) Assignee: SONY CORPORATION, Tokyo (JP)

( * ) Notice: Subject to any disclaimer, the term of this patent is extended or adjusted under 35 U.S.C. 154(b) by 54 days.

(21) Appl. No.: 16/753,703

(22) PCT Filed: Sep. 18, 2018

(86) PCT No.: PCT/JP2018/034416
§ 371 (c)(1),
(2) Date: Apr. 3, 2020

(87) PCT Pub. No.: WO2019/073756
PCT Pub. Date: Apr. 18, 2019

(65) Prior Publication Data
US 2020/0268275 A1 Aug. 27, 2020

(30) Foreign Application Priority Data
Oct. 13, 2017 (JP) .............................. JP2017-199404

(51) Int. Cl.
*A61B 5/0531* (2021.01)
*A61B 5/00* (2006.01)

(52) U.S. Cl.
CPC ............ *A61B 5/0531* (2013.01); *A61B 5/681* (2013.01); *A61B 5/7203* (2013.01); *A61B 5/7225* (2013.01)

(58) Field of Classification Search
CPC ..... A61B 5/0531; A61B 5/681; A61B 5/7203; A61B 5/7225; A61B 5/6843;
(Continued)

(56) References Cited

U.S. PATENT DOCUMENTS 10,285,620 B2 * 5/2019 Jung .................... A61B 5/6826
11,026,628 B1 * 6/2021 Bruinsma .............. A61B 5/282
(Continued)

FOREIGN PATENT DOCUMENTS

CA 2907426 A1 9/2014
CN 103006199 A 4/2013
(Continued)

OTHER PUBLICATIONS

International Search Report and Written Opinion of PCT Application No. PCT/JP2018/034416, dated Dec. 18, 2018, 14 pages of ISRWO.

(Continued)

*Primary Examiner* — Devin B Henson
*Assistant Examiner* — Justin Xu
(74) *Attorney, Agent, or Firm* — Chip Law Group

(57) ABSTRACT

A biological information measurement device according to an embodiment of the present disclosure includes a control section that controls a first connection and disconnection and a second connection and disconnection, thereby inputting, to an AD conversion section, a plurality of first analog signals for changes in impedance or conductance between electrodes of individual electrode pairs and a second analog signal for a change in impedance or conductance between the electrodes of a plurality of the electrode pairs.

7 Claims, 25 Drawing Sheets

(58) Field of Classification Search
CPC . A61B 2562/046; A61B 5/721; A61B 5/7214; A61B 5/7221; A61B 5/164; A61B 5/165; A61B 5/0537; H01H 1/58
See application file for complete search history.

(56) References Cited

U.S. PATENT DOCUMENTS

| | | | |
|---|---|---|---|
| 2013/0079619 A1 | 3/2013 | Lee et al. | |
| 2013/0317318 A1 | 11/2013 | Tartz et al. | |
| 2014/0316229 A1 | 10/2014 | Tognetti et al. | |
| 2015/0230757 A1 | 8/2015 | Ki et al. | |
| 2015/0327815 A1 | 11/2015 | Hwang | |
| 2017/0007186 A1 | 1/2017 | Baek et al. | |
| 2018/0014742 A1 | 1/2018 | Iwawaki | |
| 2018/0014784 A1* | 1/2018 | Heeger | A61B 5/6843 |

FOREIGN PATENT DOCUMENTS

| | | |
|---|---|---|
| CN | 104321016 A | 1/2015 |
| CN | 105263406 A | 1/2016 |
| CN | 107847139 A | 3/2018 |
| EP | 2572635 A2 | 3/2013 |
| EP | 2967415 A1 | 1/2016 |
| EP | 3319506 A1 | 5/2018 |
| JP | 2014-023711 A | 2/2014 |
| JP | 2015-520656 A | 7/2015 |
| JP | 2016-516461 A | 6/2016 |
| JP | 2016-152624 A | 8/2016 |
| JP | 2016-154754 A | 9/2016 |
| JP | 2018-522637 A | 8/2018 |
| KR | 10-2015-0023466 A | 3/2015 |
| KR | 10-2015-0097167 A | 8/2015 |
| KR | 10-2015-0130057 A | 11/2015 |
| KR | 10-2018-0027500 A | 3/2018 |
| WO | 2013/177451 A1 | 11/2013 |
| WO | 2014/147024 A1 | 9/2014 |
| WO | 2016/136135 A1 | 9/2016 |
| WO | 2016/149831 A1 | 9/2016 |
| WO | 2017/007574 A1 | 1/2017 |

OTHER PUBLICATIONS

Extended European Search Report of EP Application No. 18865975.9, dated Feb. 9, 2021, 14 pages.

Office Action for JP Patent Application No. 2019-547960, dated May 10, 2022, 03 pages of English Translation and 33 pages of Office Action.

* cited by examiner

[FIG. 1]
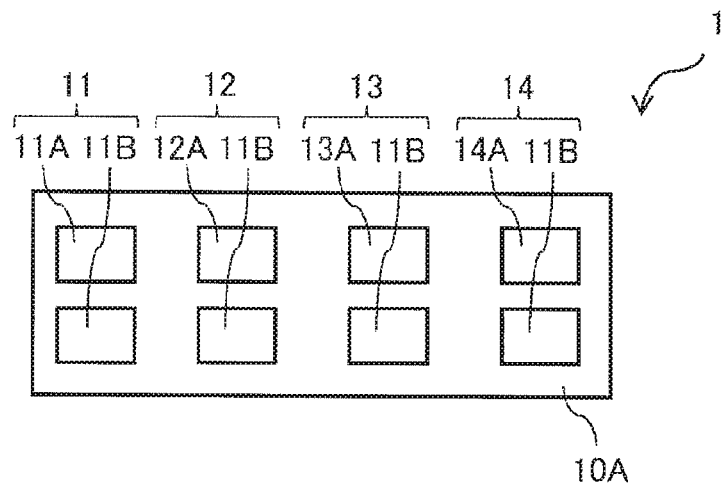
[FIG. 2]
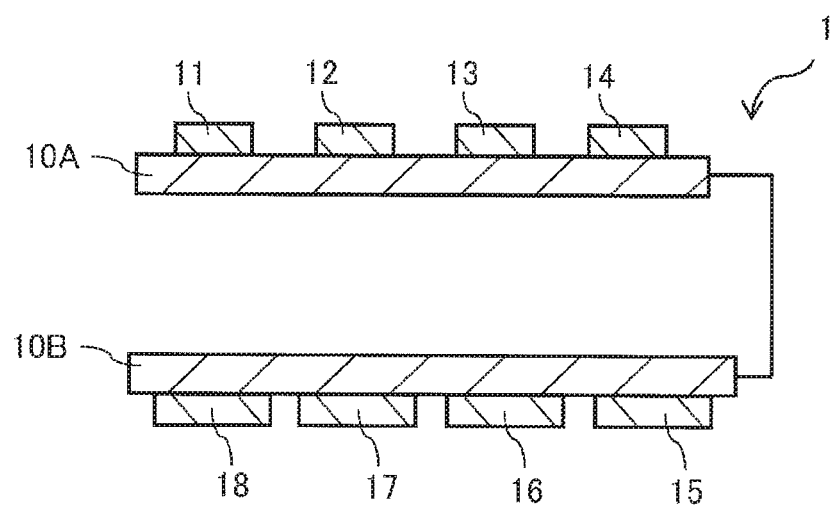
[FIG. 3]
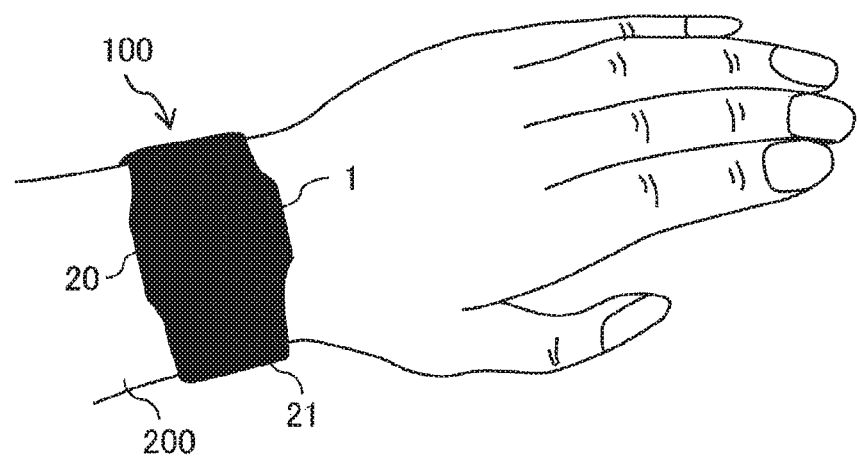

[FIG. 4]
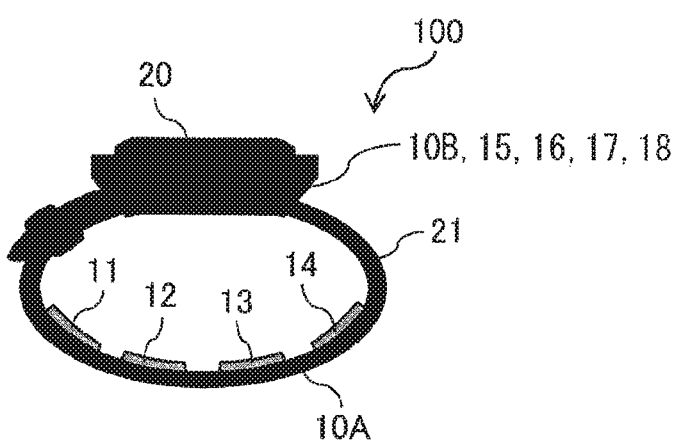

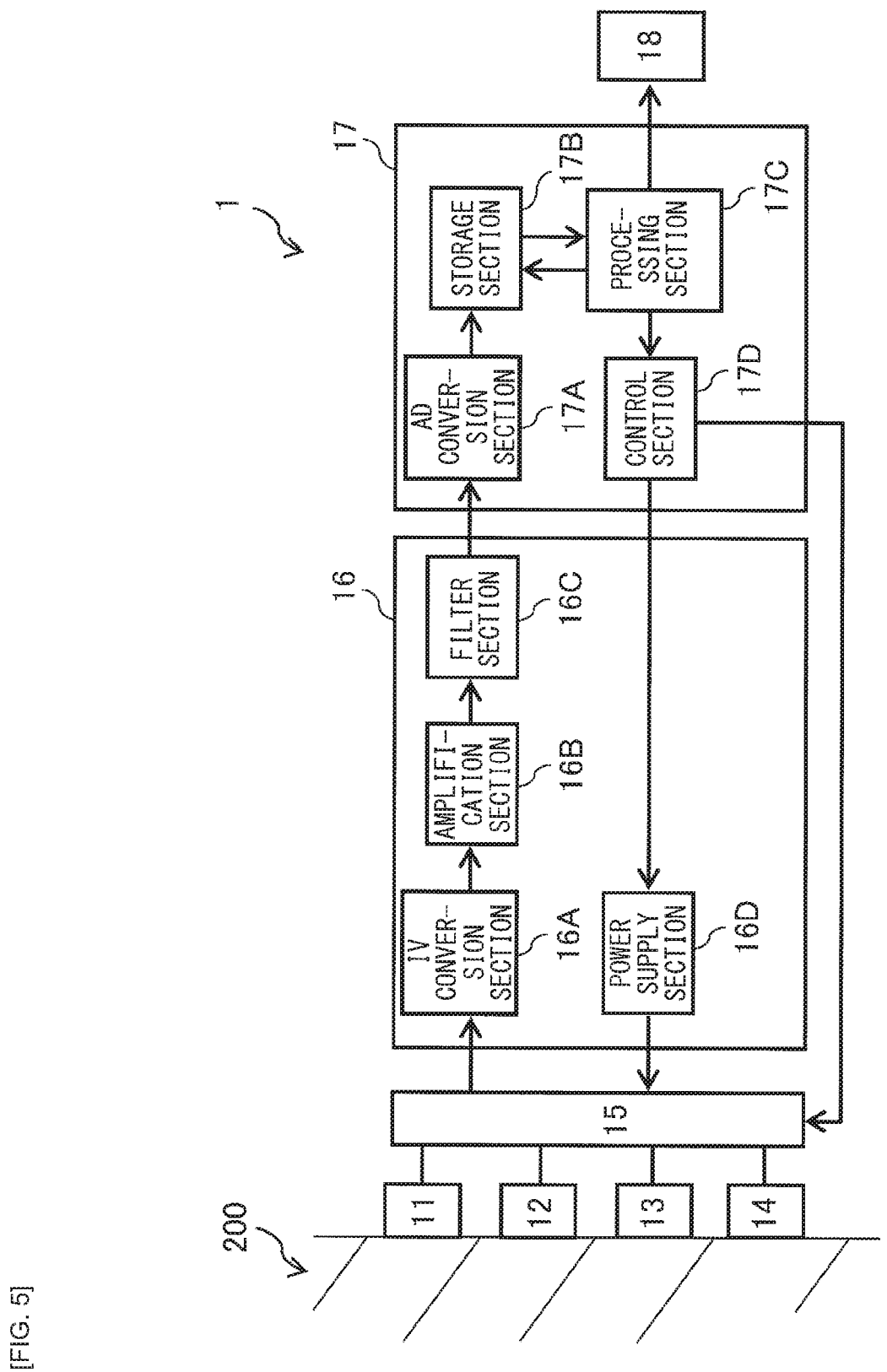
[FIG. 5]

[FIG. 6]
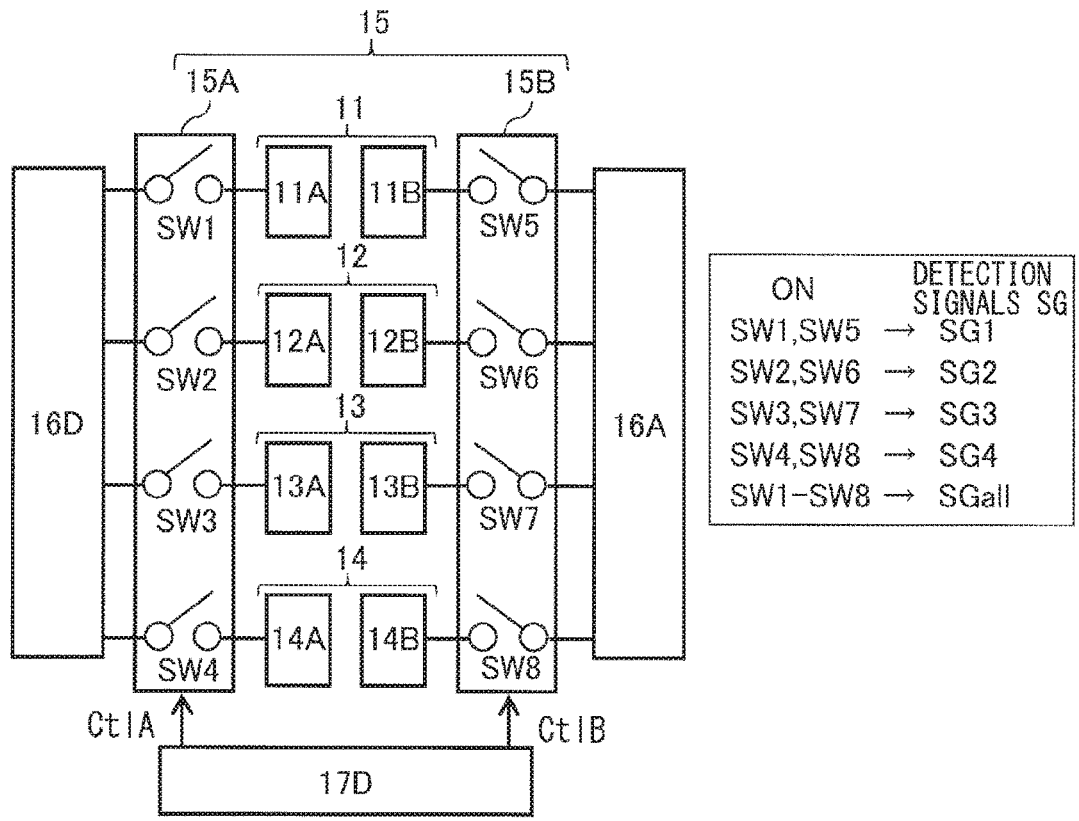
[FIG. 7]
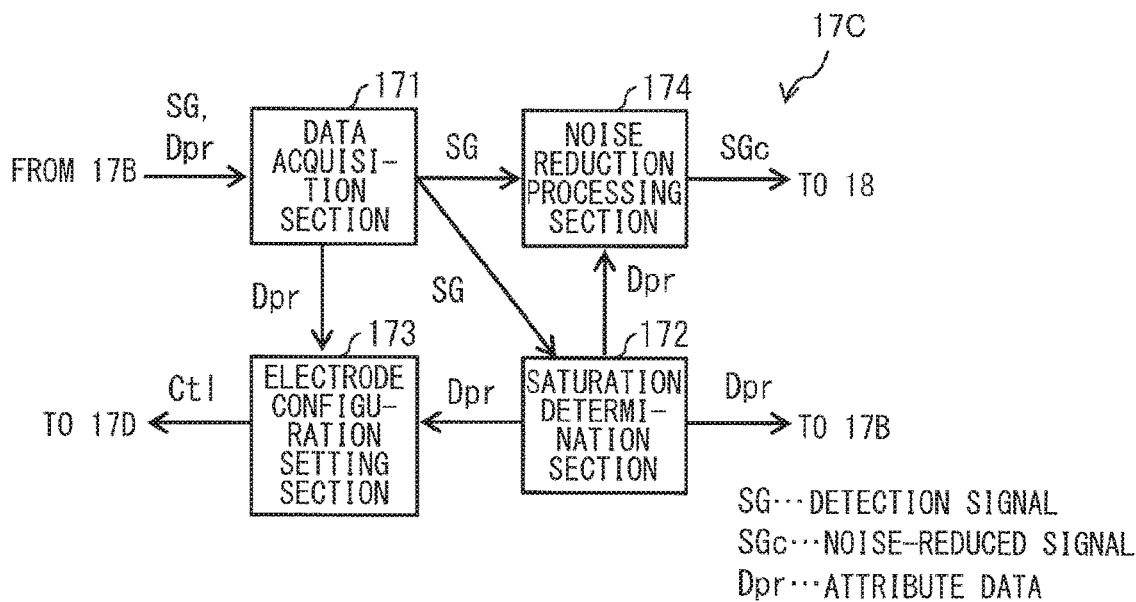

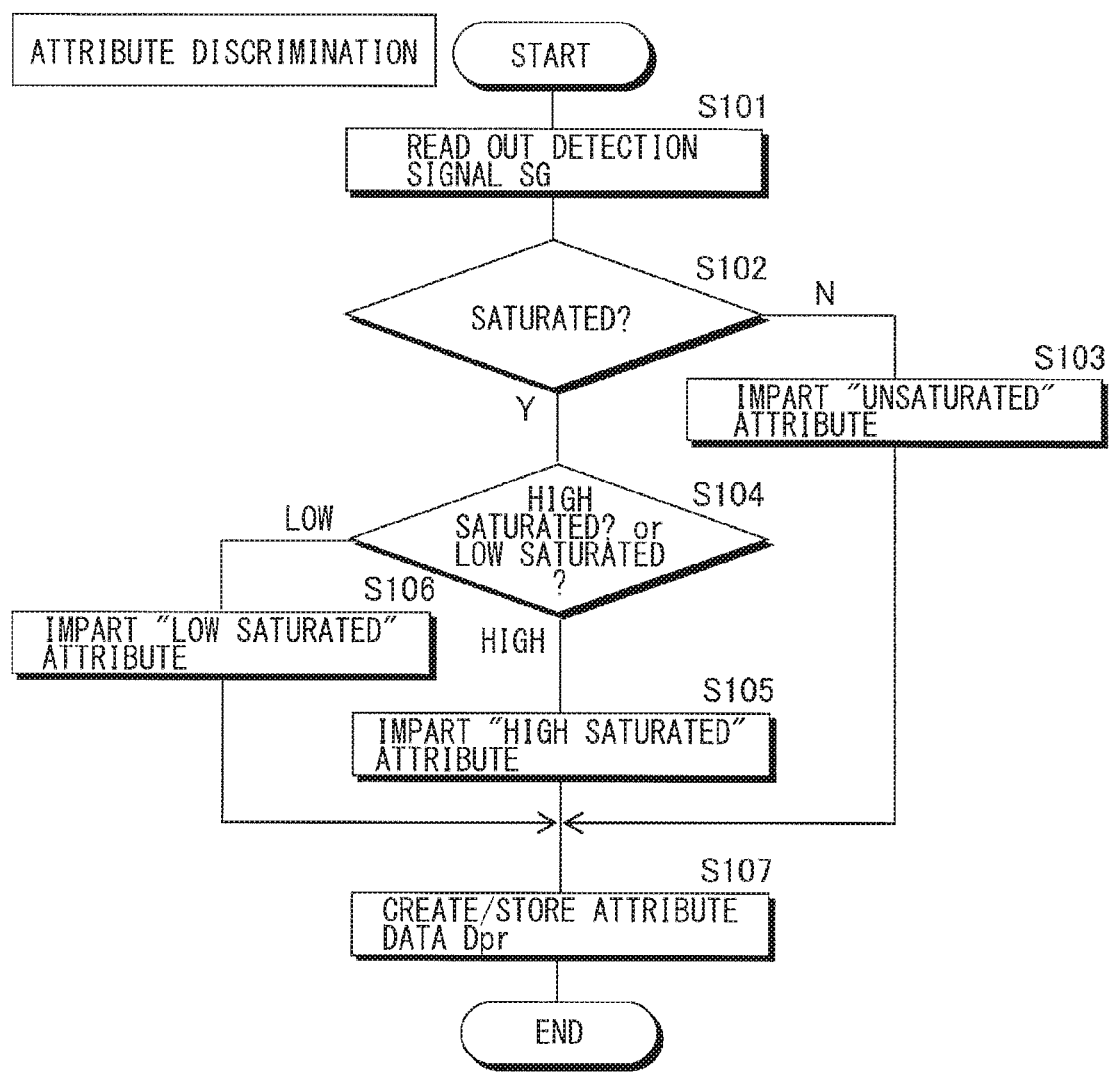
[FIG. 8]

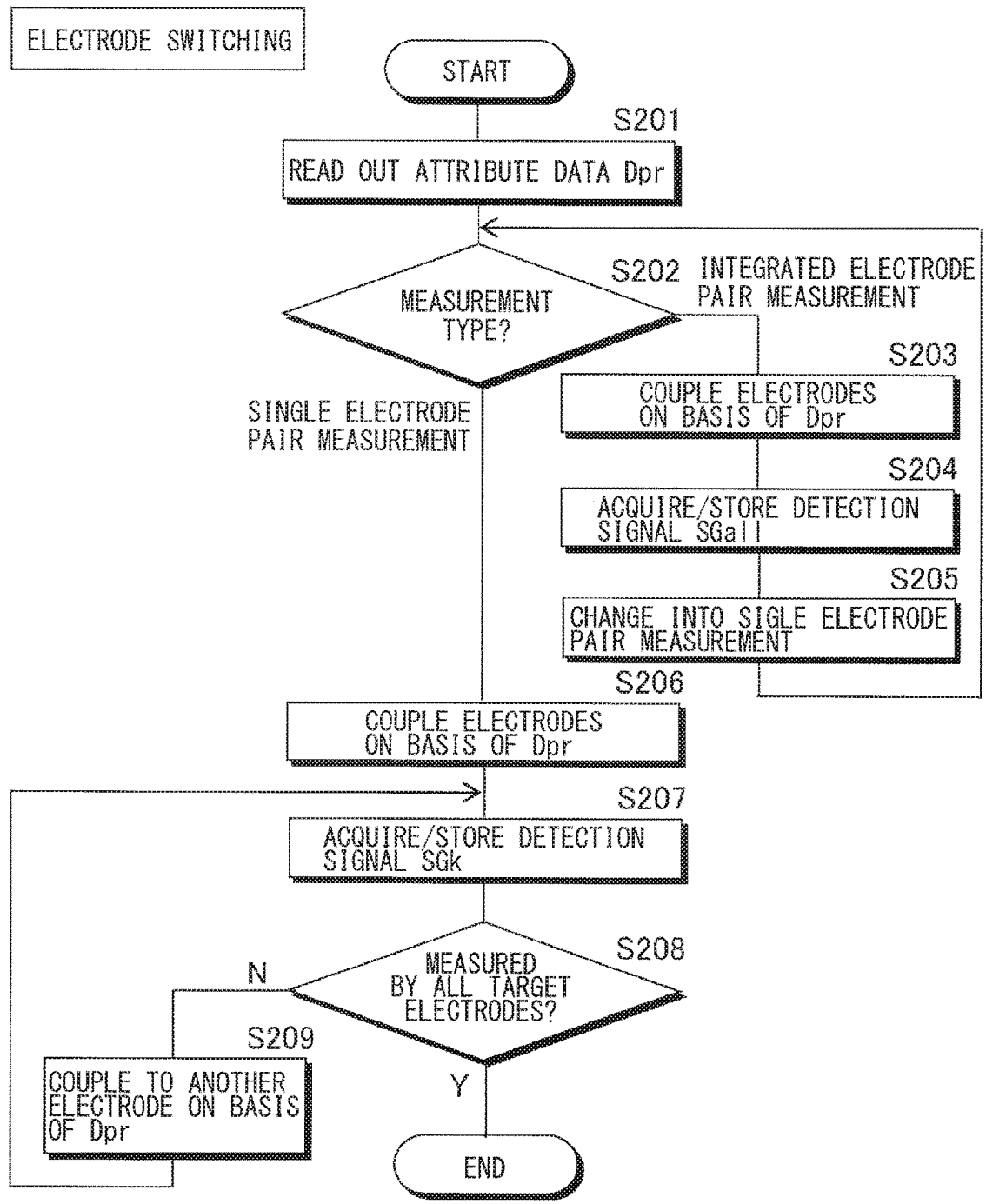
[FIG. 9]

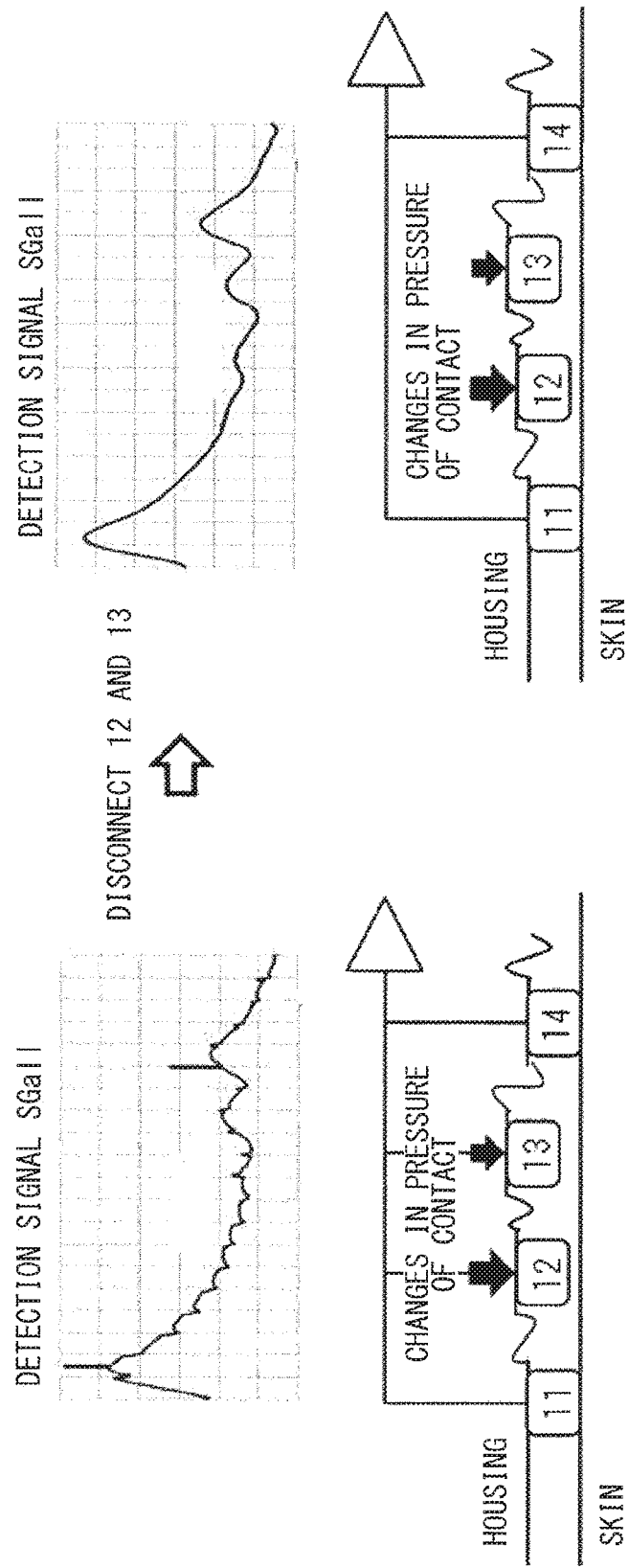

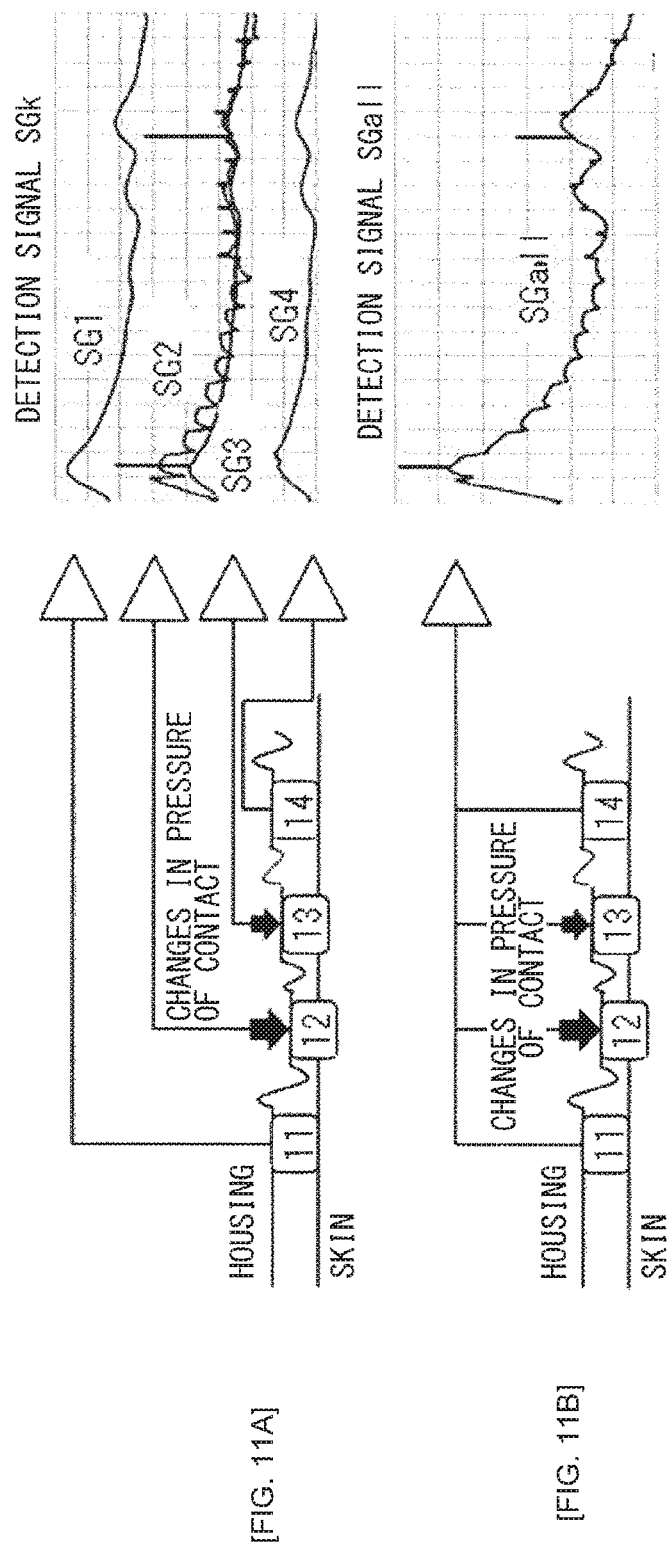

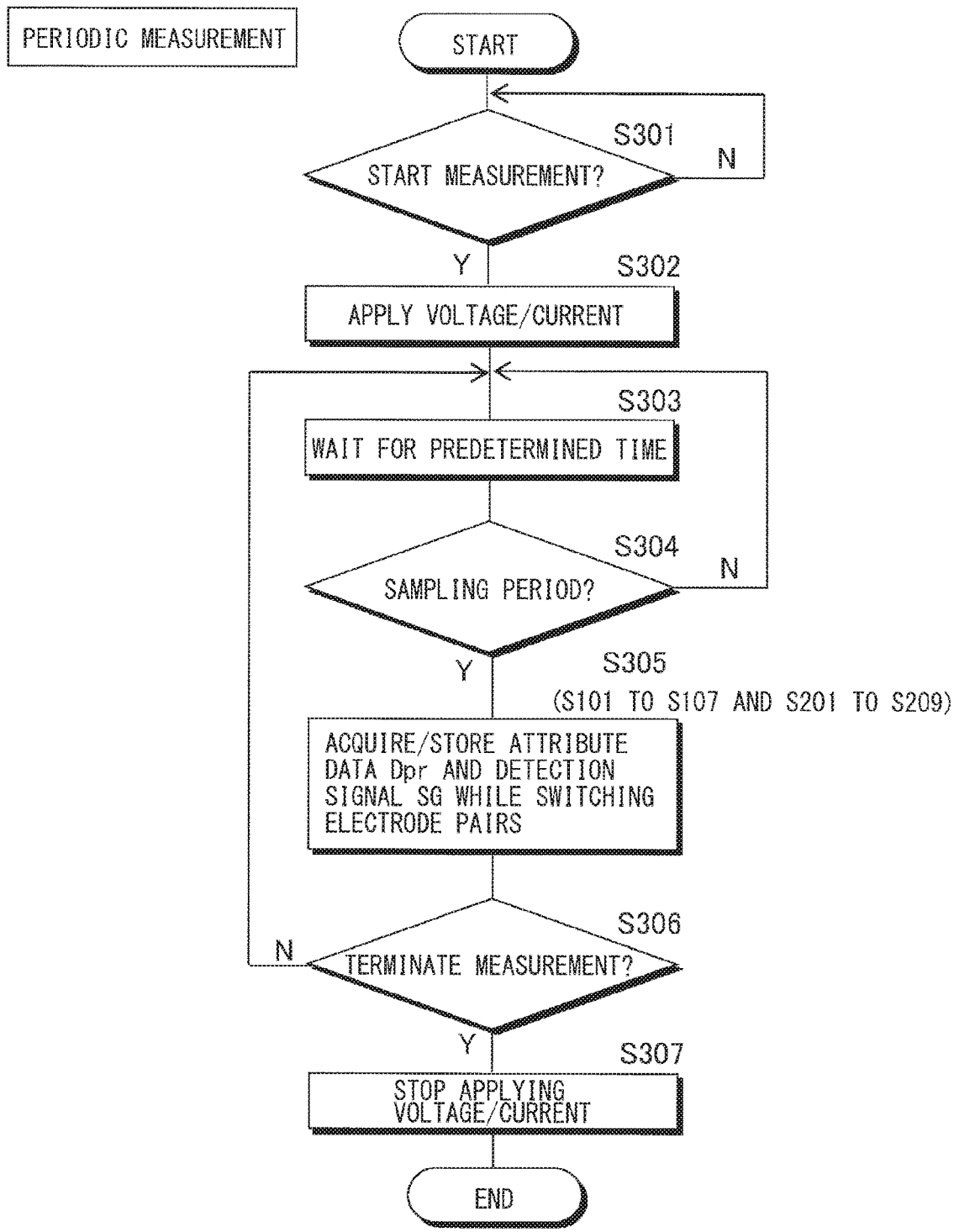

[FIG. 13]
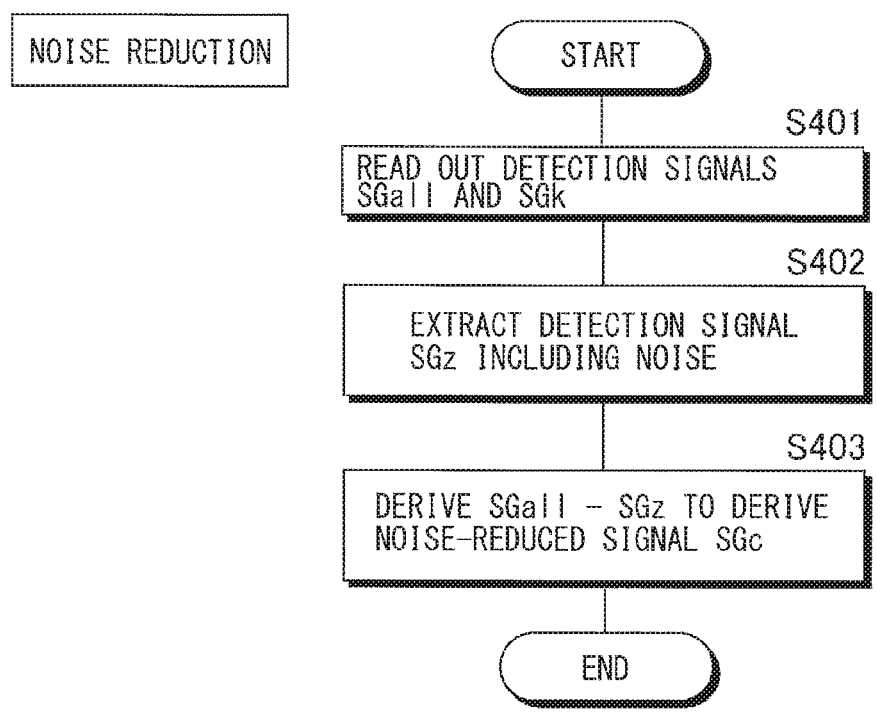

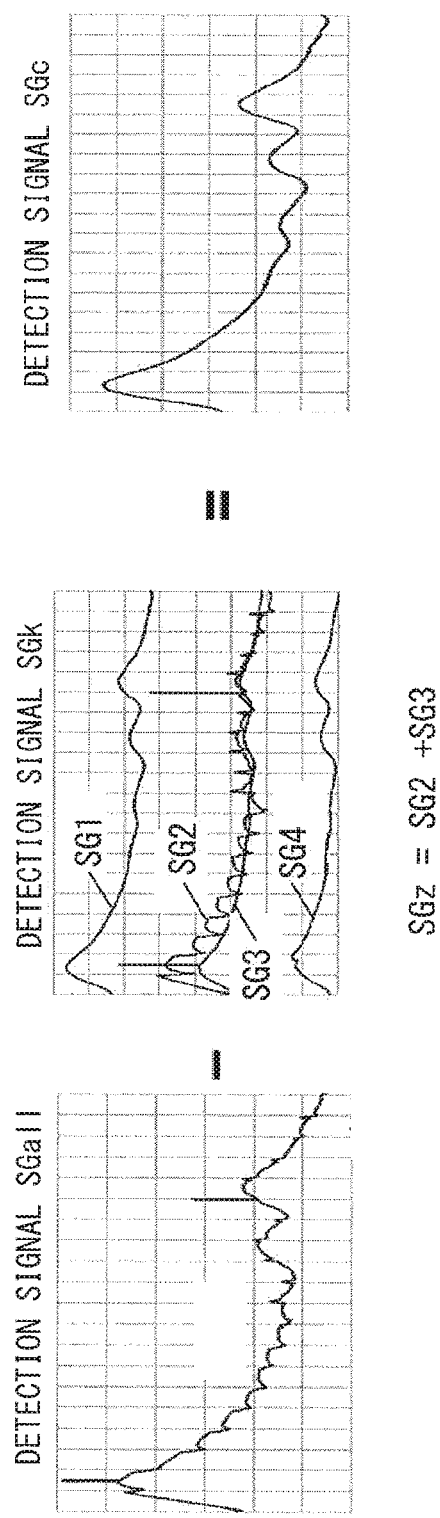
[FIG. 14]

[FIG. 15]
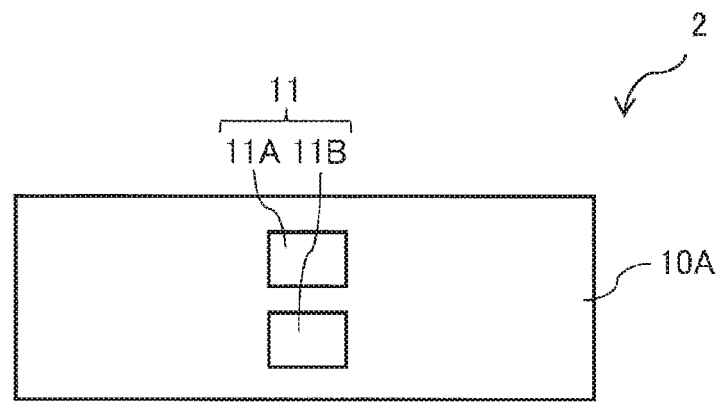
[FIG. 16]
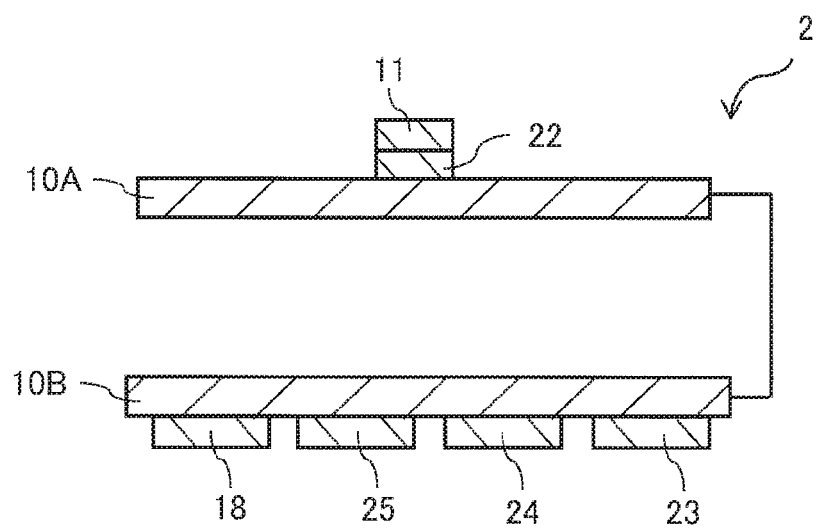
[FIG. 17]
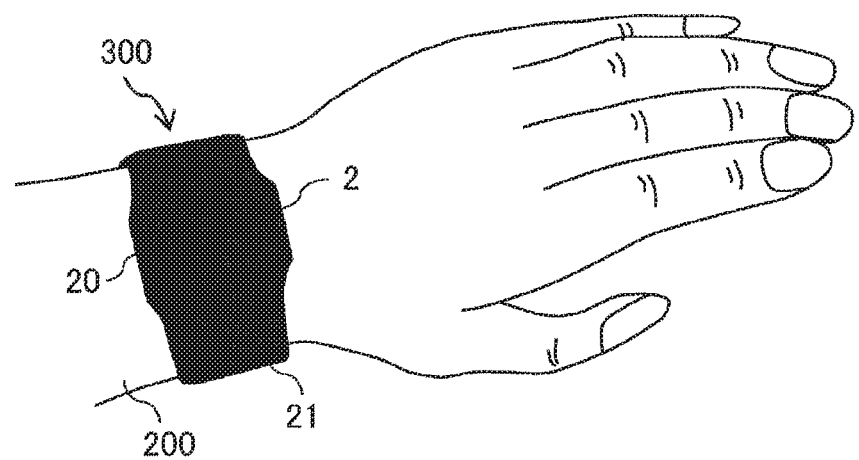

[FIG. 18]
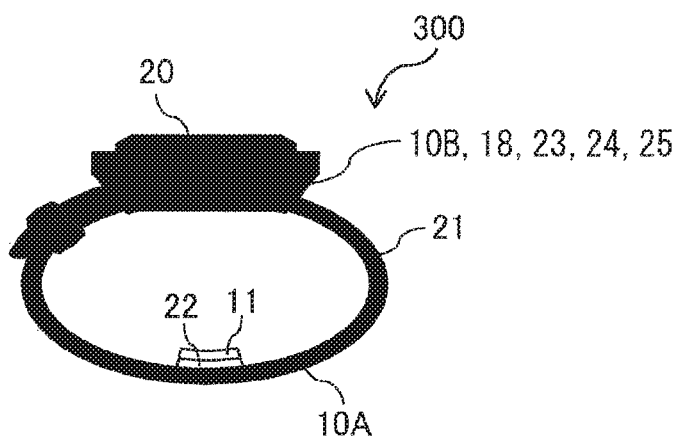

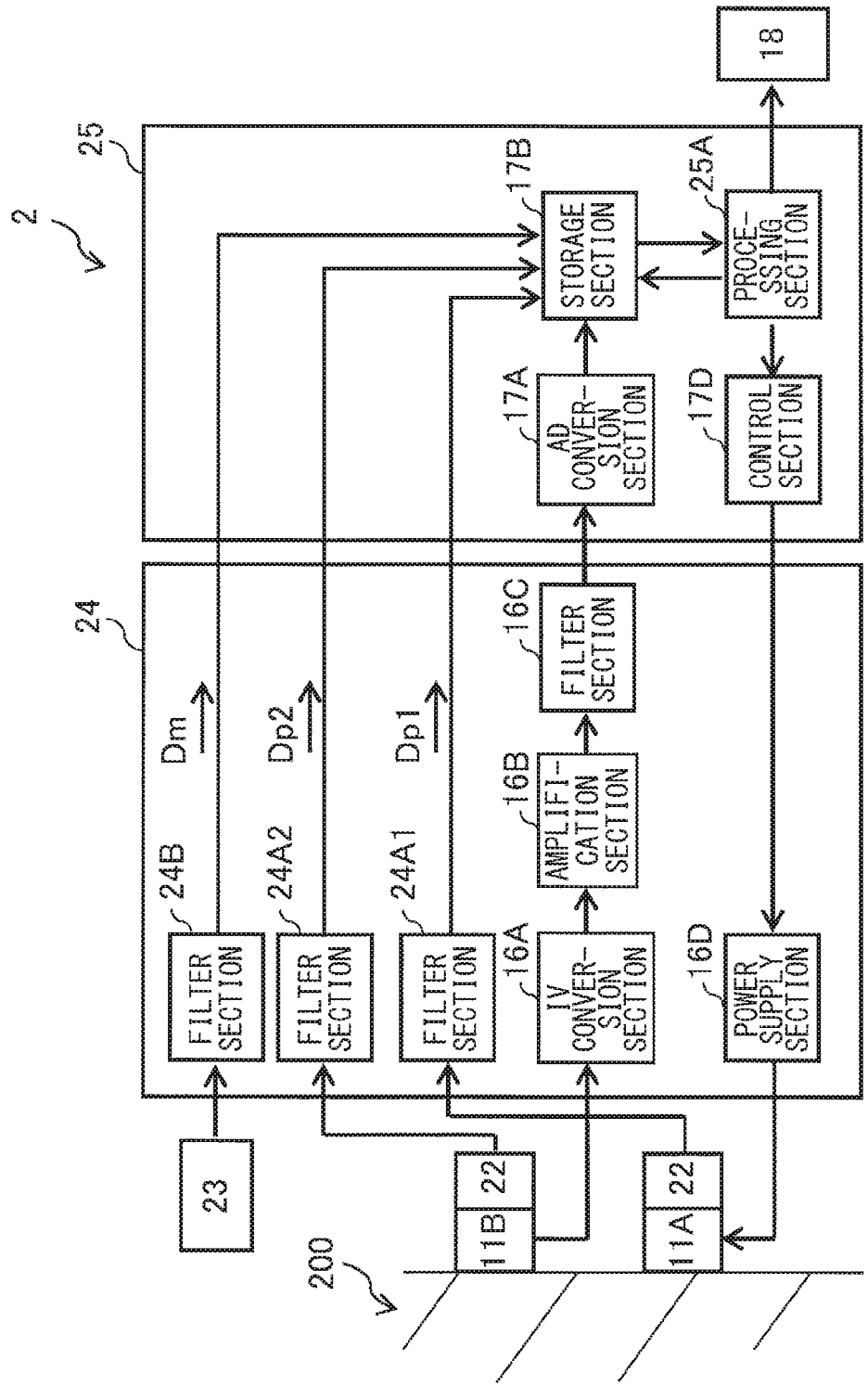
[FIG. 19]

[FIG. 20]
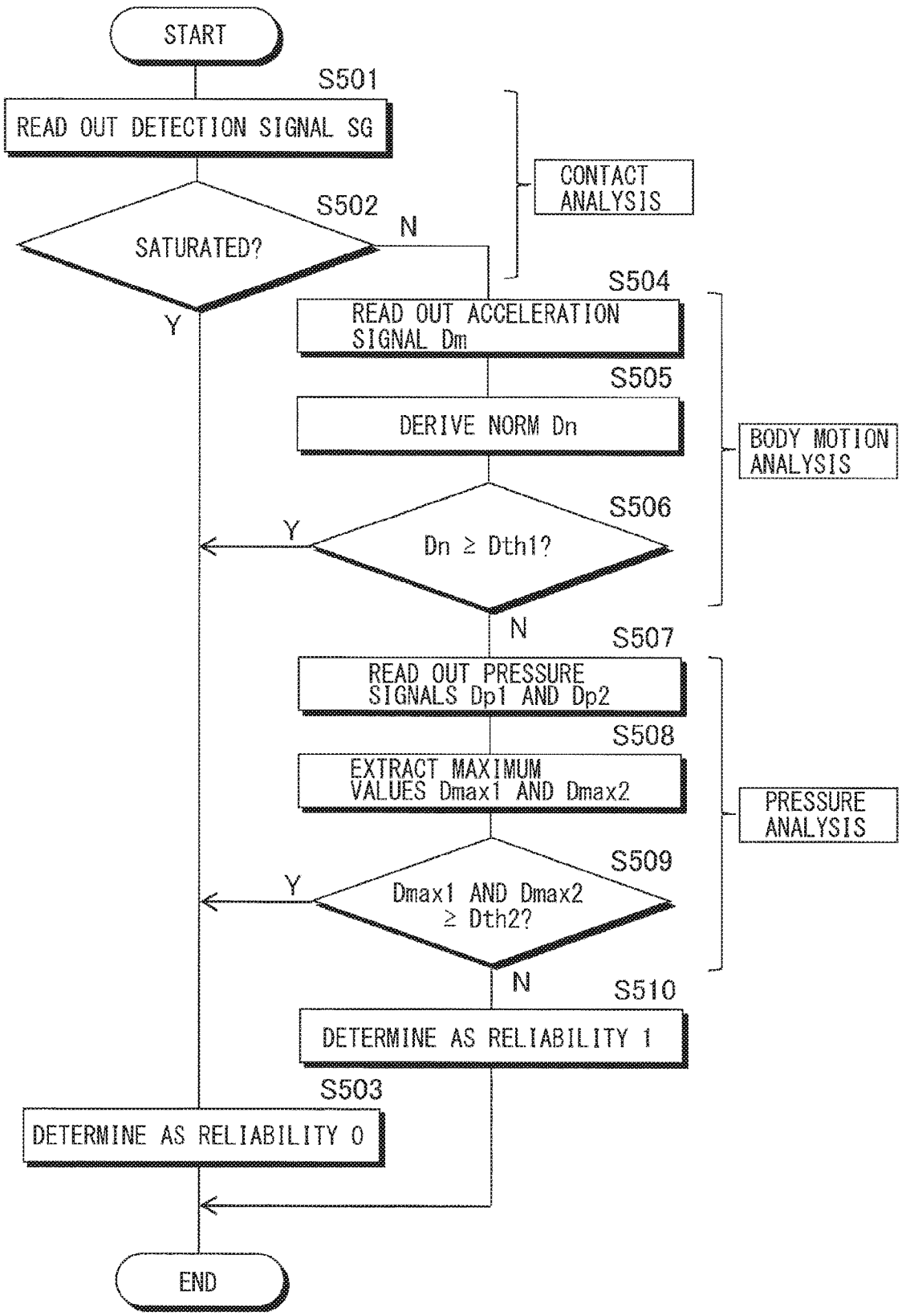

[FIG. 21]
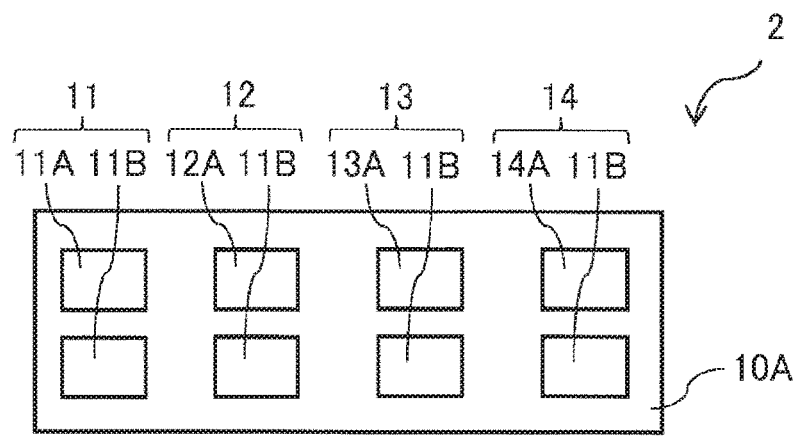
[FIG. 22]
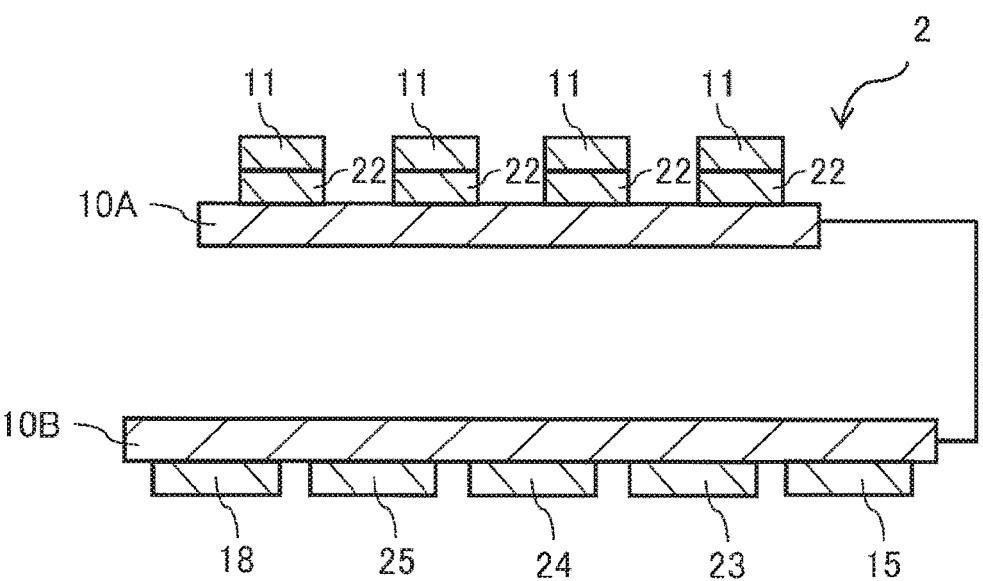
[FIG. 23]
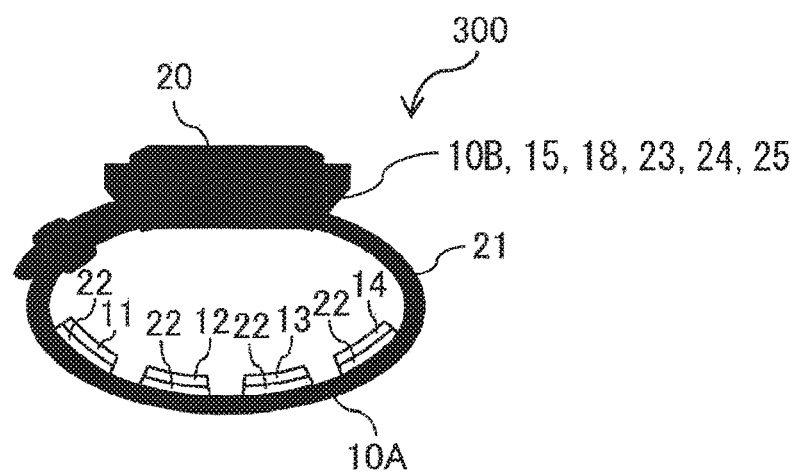

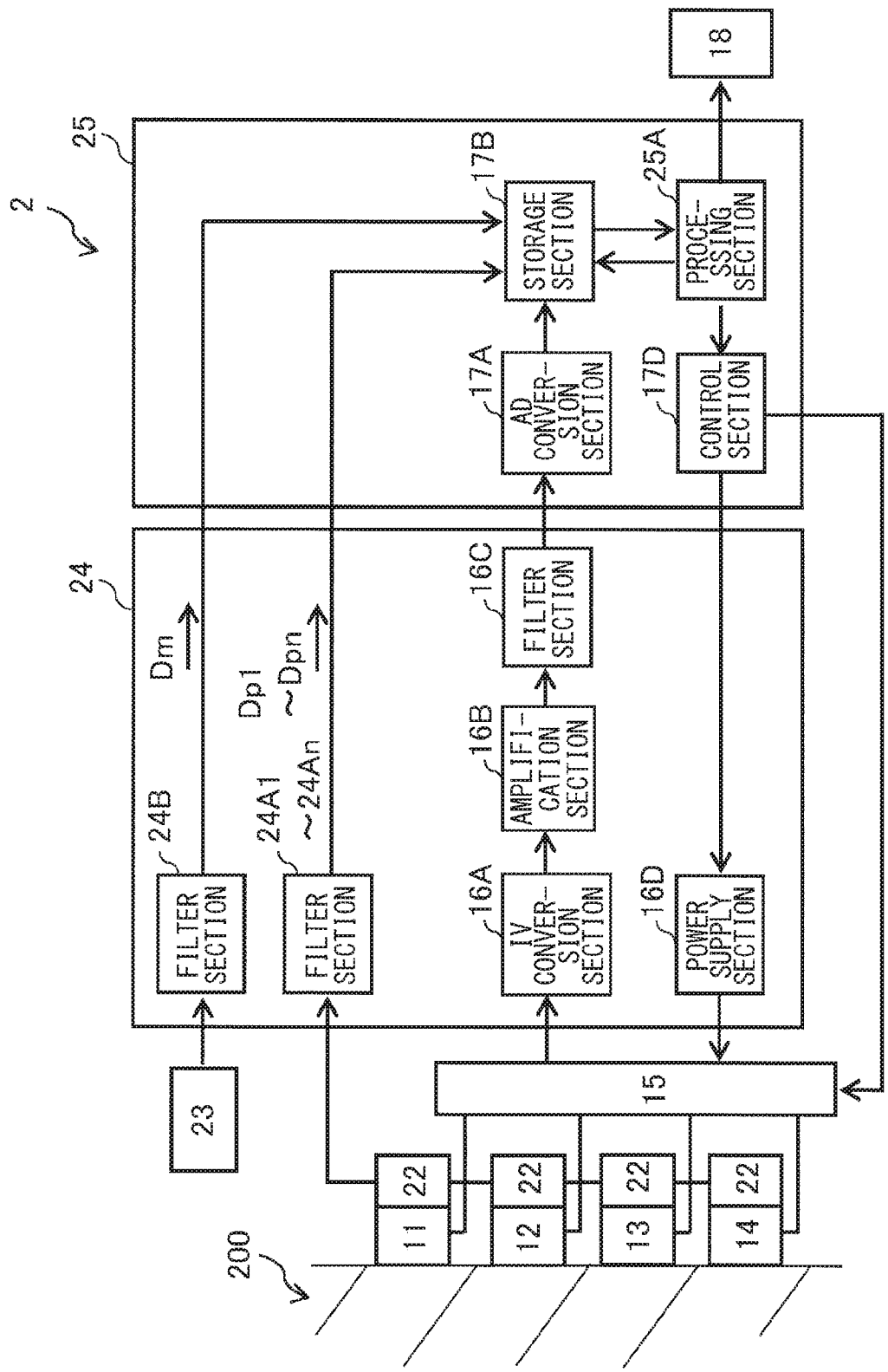
[FIG. 24]

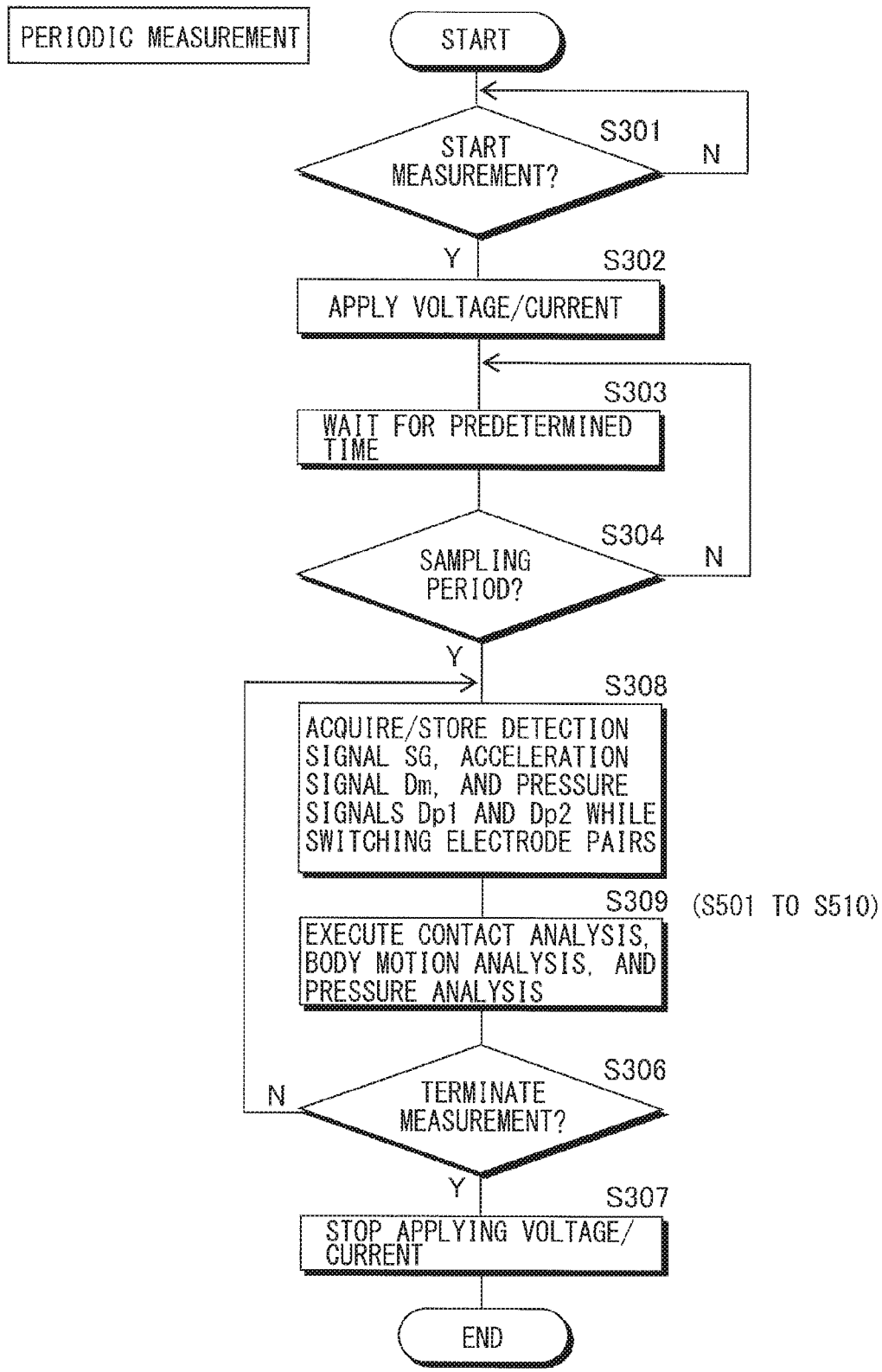
[FIG. 25]

[FIG. 26]
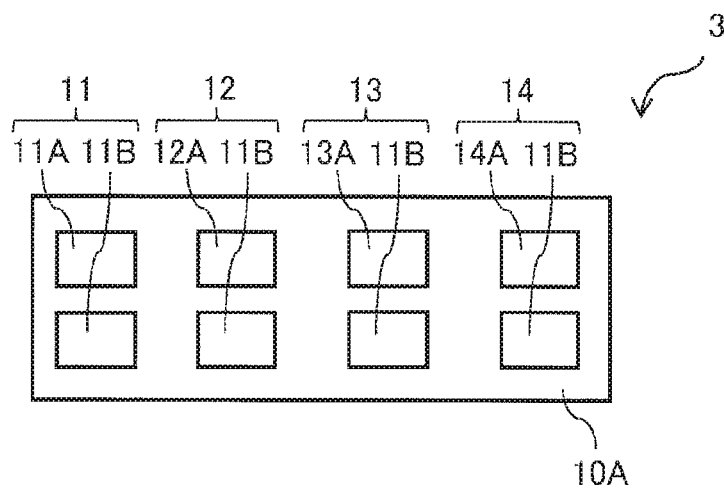
[FIG. 27]
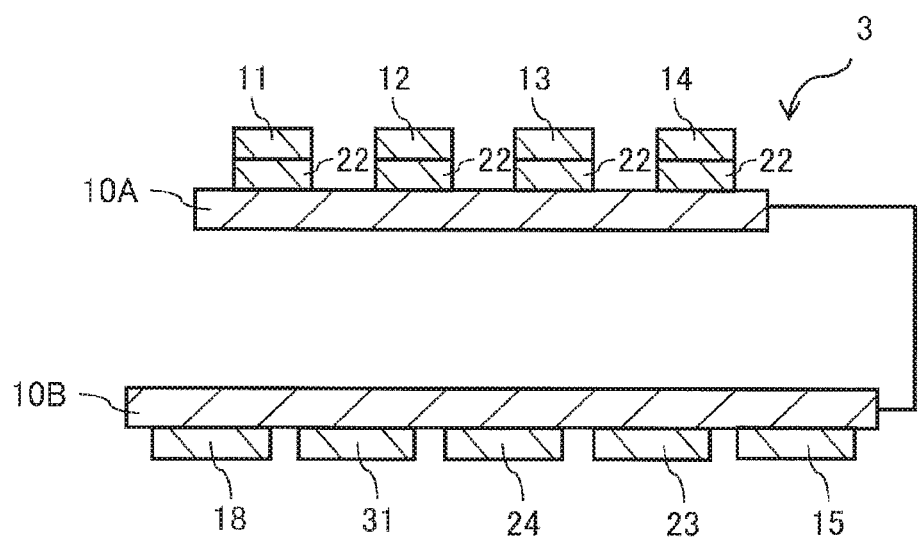
[FIG. 28]
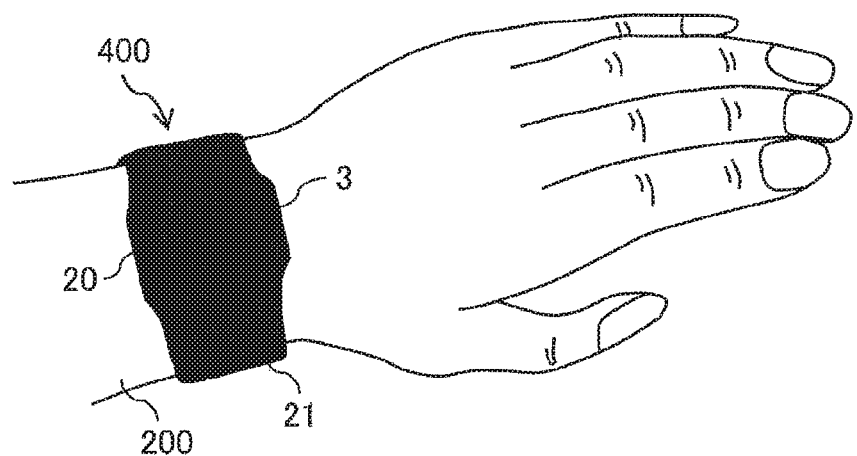

[FIG. 29]
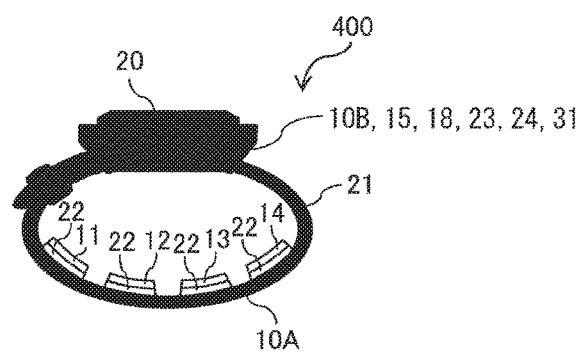

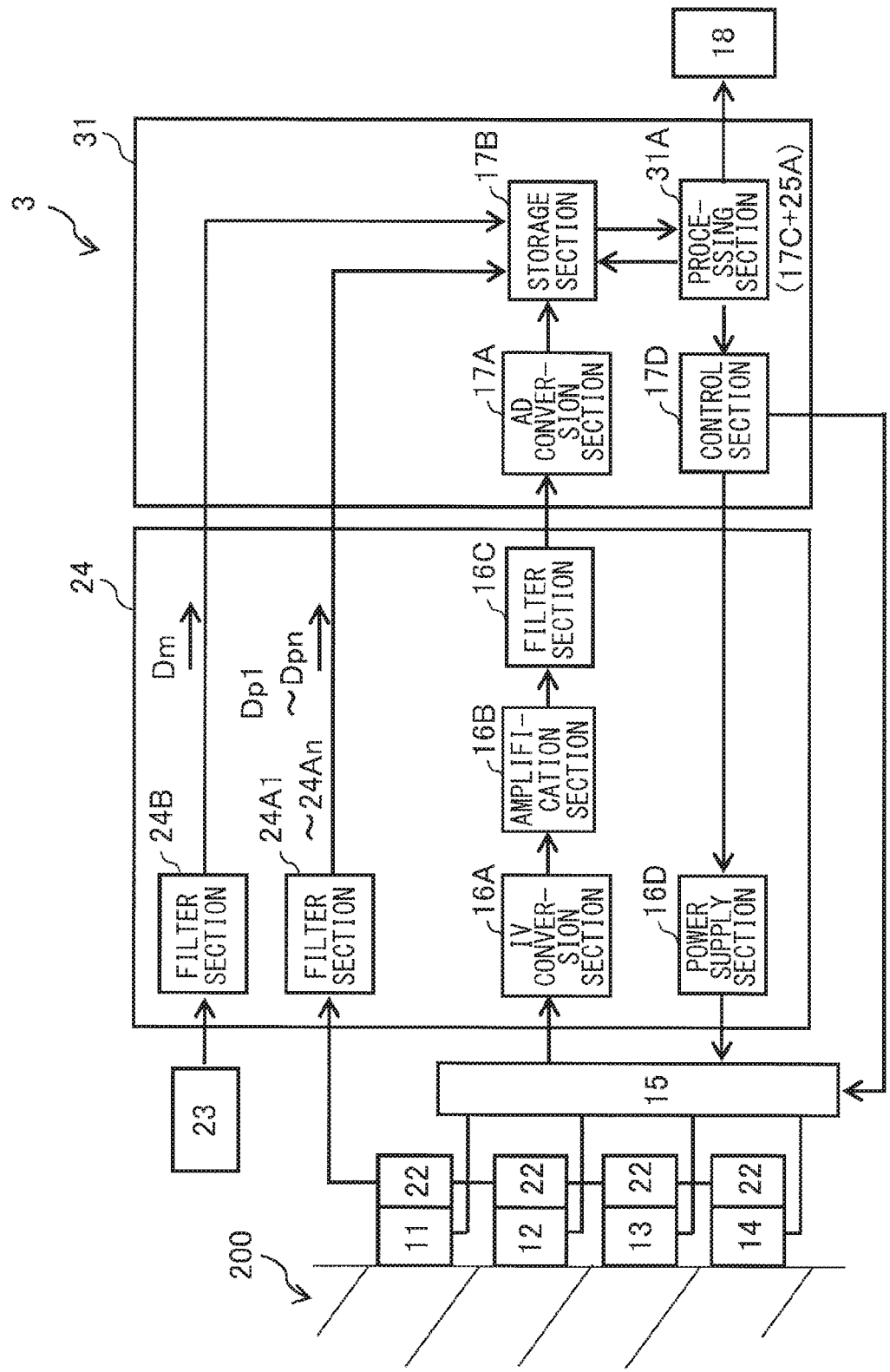
[FIG. 30]

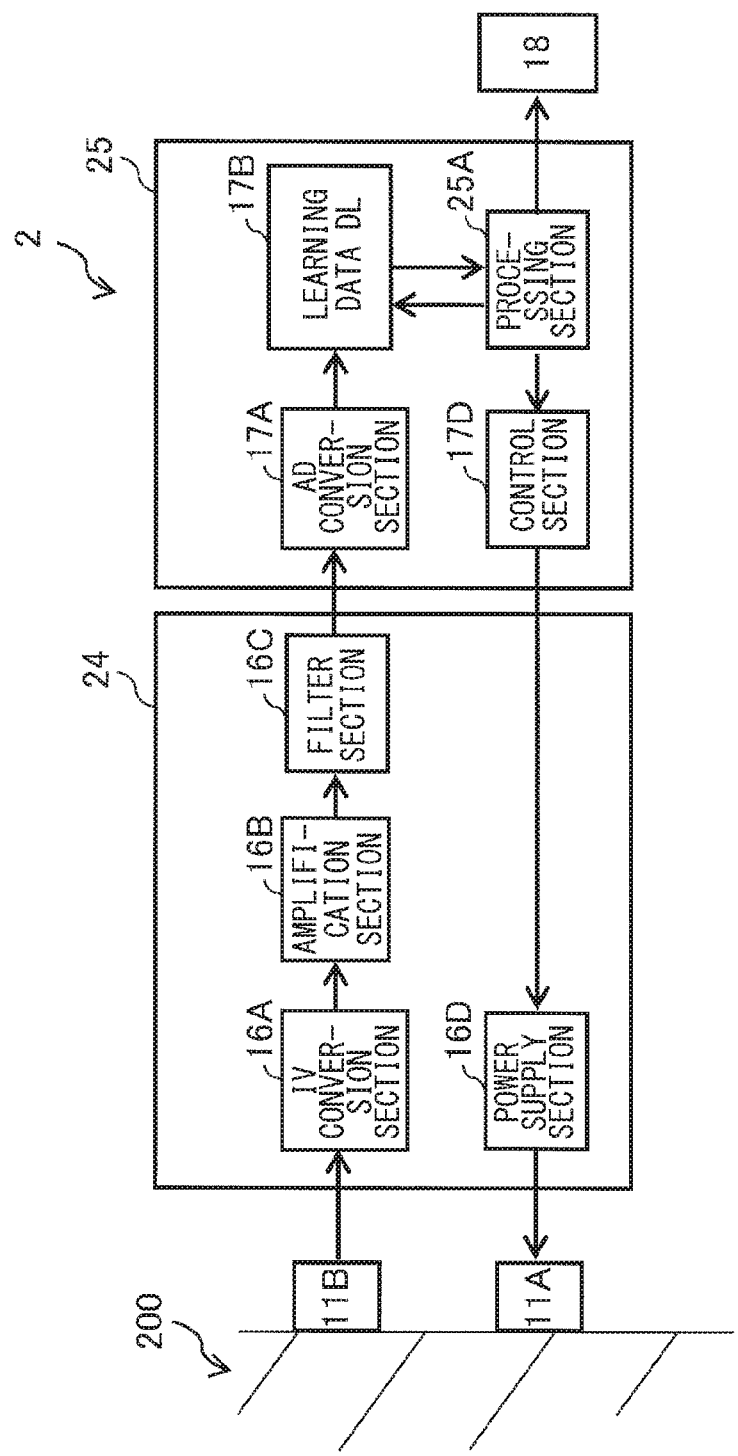
[FIG. 31]

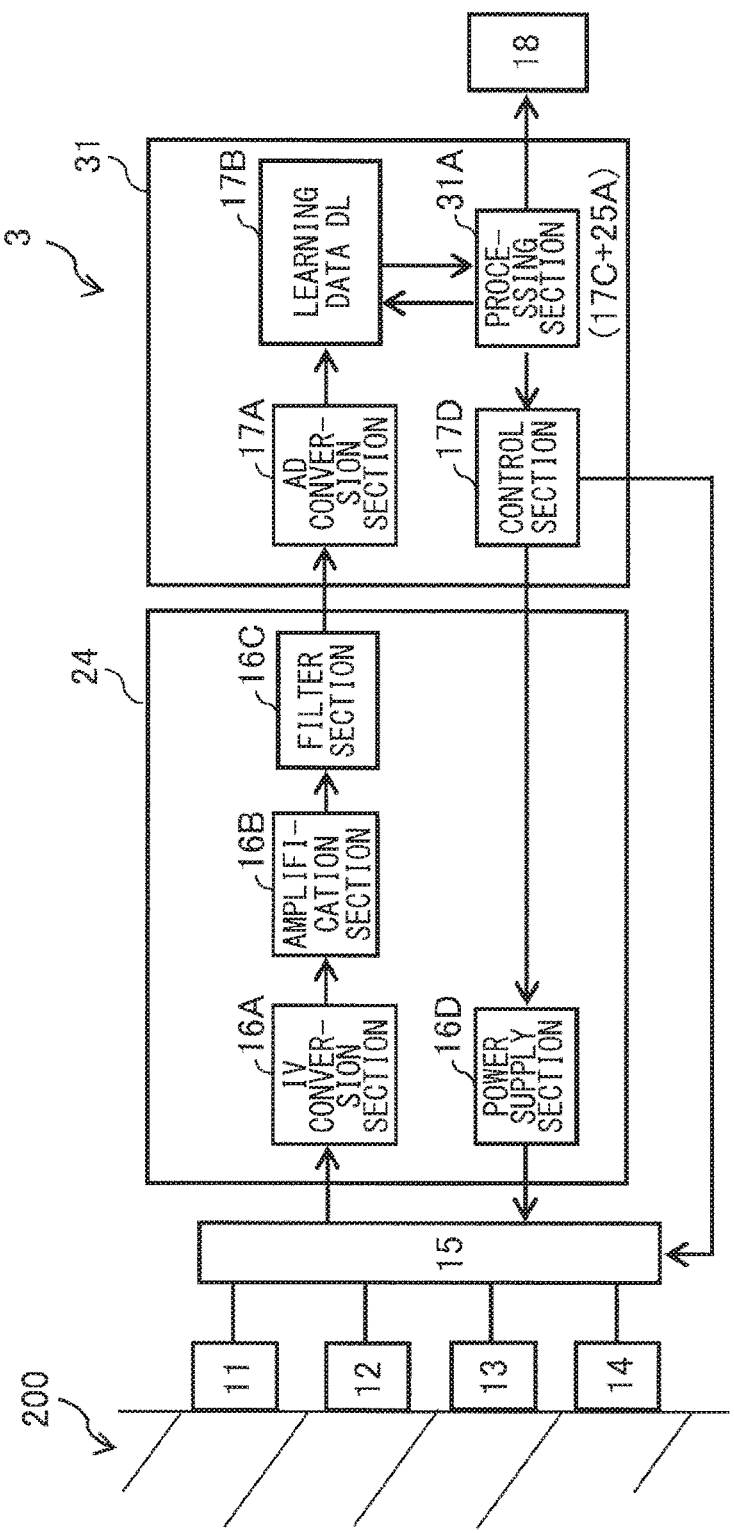
[FIG. 32]

[FIG. 33]
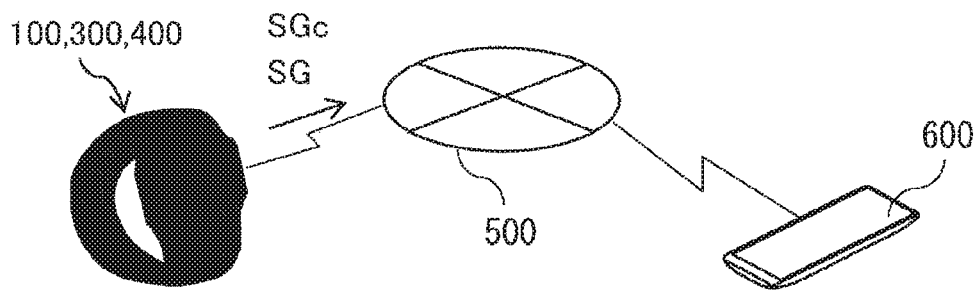
[FIG. 34]
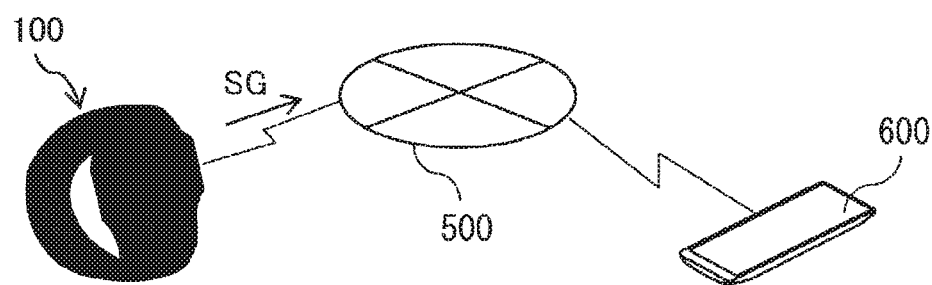
[FIG. 35]
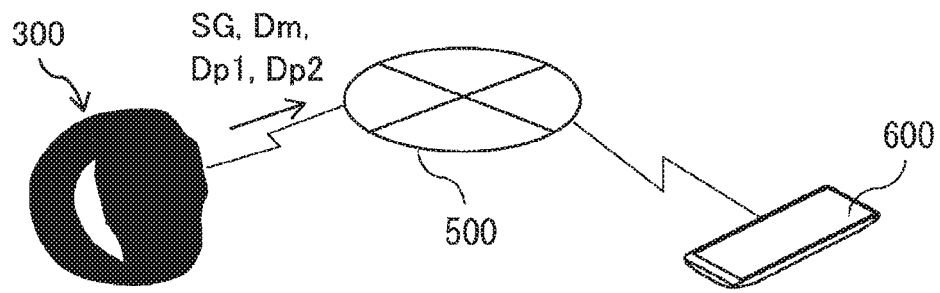
[FIG. 36]
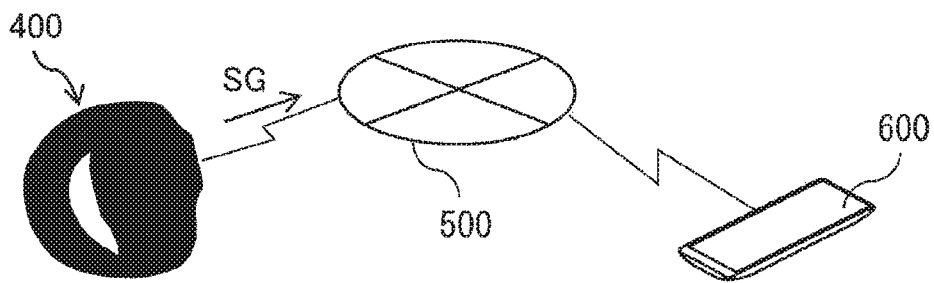

[FIG. 37]
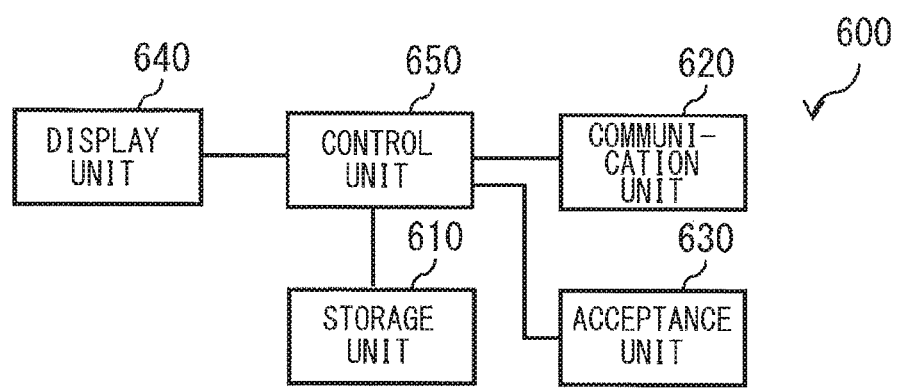

BIOLOGICAL INFORMATION MEASUREMENT DEVICE AND BIOLOGICAL INFORMATION MEASUREMENT SYSTEM

CROSS REFERENCE TO RELATED APPLICATIONS

This application is a U.S. National Phase of International Patent Application No. PCT/JP2018/034416 filed on Sep. 18, 2018, which claims priority benefit of Japanese Patent Application No. JP 2017-199404 filed in the Japan Patent Office on Oct. 13, 2017. Each of the above-referenced applications is hereby incorporated herein by reference in its entirety.

TECHNICAL FIELD

The present disclosure relates to a biological information measurement device and a biological information measurement system.

BACKGROUND ART

In recent years, as wearable devices have evolved and constant wireless access has been gaining widespread use, devices mounted with sensors that sense biological information have been developed.

CITATION LIST

Patent Literature

PTL 1: Japanese Unexamined Patent Application Publication (Published Japanese Translation of PCT Application) No. JP 2015-520656
PTL 2: Japanese Unexamined Patent Application Publication No. 2016-516461
PTL 3: Japanese Unexamined Patent Application Publication No. 2014-23711

SUMMARY OF THE INVENTION

Problems to be Solved by the Invention

Incidentally, the field of wearable devices mounted with sensors that sense biological information requires biological information having less noise or requires the noise included in biological information to be decreased. It is thus desirable to provide a biological information measurement device and a biological information measurement system each of which allows biological information having less noise to be acquired or allows the noise included in biological information to be decreased.

A first biological information measurement device according to an embodiment of the present disclosure includes a plurality of electrode pairs that is brought into contact with skin; and a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section. The control section controls the first connection and disconnection and the second connection and disconnection, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs. The first biological information measurement device further includes a processing section that derives a noise-reduced signal in which noise included in the second digital signal is reduced, on the basis of a plurality of first digital signals and the second digital signal. The plurality of first digital signals is obtained by converting the plurality of first analog signals by the AD conversion section. The second digital signal is obtained by converting the second analog signal by the AD conversion section.

A first biological information measurement system according to an embodiment of the present disclosure includes a wearable apparatus; and an external apparatus. The wearable apparatus includes a plurality of electrode pairs that is brought into contact with skin; and a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section. The control section controls the first connection and disconnection and the second connection and disconnection, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs. The wearable apparatus further includes a processing section that derives a noise-reduced signal in which noise included in the second digital signal is reduced, on the basis of a plurality of first digital signals and the second digital signal. The plurality of first digital signals is obtained by converting the plurality of first analog signals by the AD conversion section. The second digital signal is obtained by converting the second analog signal by the AD conversion section. Moreover, the wearable apparatus further includes a transmission unit that transmits the noise-reduced signal to the external apparatus. The noise-reduced signal is derived by the processing section. The external apparatus includes a reception unit that receives the noise-reduced signal from the transmission unit.

A second biological information measurement system according to an embodiment of the present disclosure includes a wearable apparatus; and an external apparatus. The wearable apparatus includes a plurality of electrode pairs that is brought into contact with skin; and a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section. The control section controls the first connection and disconnection and the second connection and disconnection, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs. The wearable apparatus further includes a transmission unit that transmits a plurality of first digital signals and a second digital signal to the external apparatus. The plurality of first digital signals is obtained by converting a plurality of the first analog signals by the AD conversion section. The second digital signal is obtained by converting the second analog signal by the AD conversion section. The external apparatus includes a reception unit that receives the plurality of the first digital signals and the second digital signal from the transmission unit. The external apparatus further includes a processing section that derives a noise-reduced signal in which noise included in the second digital signal is reduced, on the basis of a plurality of the first digital signals and the second digital signal received by the reception unit.

The first biological information measurement device, first biological information measurement system, and second biological information measurement system according to an embodiment of the present disclosure derive the noise-reduced signal in which the noise included in the second digital signal is reduced, on the basis of a plurality of the first analog signals for changes in impedance or conductance between the electrodes of the individual electrode pairs and the second analog signal for a change in impedance or conductance between the electrodes of a plurality of the electrode pairs. This reduces noise without using a noise reference obtained from another sensor. The noise is caused by changes in pressure of contact between the electrodes and the skin.

A second biological information measurement device according to an embodiment of the present disclosure includes a plurality of electrode pairs that is brought into contact with skin; a power supply section that supplies one or more electrode pairs with power; and an acquisition section that acquires one or more biological signals for changes in impedance or conductance between electrodes of the one or more electrode pairs. The second biological information measurement device further includes a determination section that determines reliability of the one or more biological signals on the basis of reference data for a state of contact of the one or more electrode pairs with the skin, a body motion state of a user, and a state of pressure of the one or more electrode pairs on the skin. The one or more biological signals are acquired by the acquisition section.

A third biological information measurement system according to an embodiment of the present disclosure includes a wearable apparatus; and an external apparatus. The wearable apparatus includes one or more electrode pairs that are brought into contact with skin; a power supply section that supplies the one or more electrode pairs with power; and an acquisition section that acquires one or more biological signals for changes in impedance or conductance between electrodes of the one or more electrode pairs. The wearable apparatus further includes a determination section that determines reliability of the one or more biological signals on the basis of reference data for a state of contact of the one or more electrode pairs with the skin, a body motion state of a user, and a state of pressure of the one or more electrode pairs on the skin. The one or more biological signals are acquired by the acquisition section. The external apparatus includes a reception unit that receives a determination result from the transmission unit.

A fourth biological information measurement system according to an embodiment of the present disclosure includes a wearable apparatus; and an external apparatus. The wearable apparatus includes one or more electrode pairs that are brought into contact with skin; a power supply section that supplies the one or more electrode pairs with power; and an acquisition section that acquires one or more biological signals for changes in impedance or conductance between electrodes of the one or more electrode pairs. The wearable apparatus further includes a transmission unit that transmits the one or more biological signals to the external apparatus. The one or more biological signals are acquired by the acquisition section. The external apparatus includes a reception unit that receives the one or more biological signals from the transmission unit. The external apparatus further includes a determination section that determines reliability of the one or more biological signals on the basis of reference data for a state of contact of the one or more electrode pairs with the skin, a body motion state of a user, and a state of pressure of the one or more electrode pairs on the skin. The one or more biological signals are received by the reception unit.

The second biological information measurement device, third biological information measurement system, and fourth biological information measurement system according to an embodiment of the present disclosure determine the reliability of the one or more biological signals on the basis of the reference data for the state of the contact of the one or more electrode pairs with the skin, the body motion state of the user, and the state of the pressure of the one or more electrode pairs on the skin. The one or more biological signals are acquired by the acquisition section. Here, the reference data are, for example, data that are obtained through learning or data that are obtained by a sensor. The use of the reference data thus allows biological signals to be extracted that have less noise caused by changes in pressure of contact between the electrodes and the skin.

The first biological information measurement device, first biological information measurement system, and second biological information measurement system according to an embodiment of the present disclosure reduce noise caused by the changes in the pressure of the contact between the electrodes and the skin without using a noise reference obtained from another sensor, making it possible to decrease the noise included in the biological information.

The second biological information measurement device, third biological information measurement system, and fourth biological information measurement system according to an embodiment of the present disclosure use the reference data to allow the biological signals to be extracted that have less noise caused by the changes in the pressure of the contact between the electrodes and the skin. This makes it possible to acquire the biological information having less noise.

It is to be noted that the effects of the present disclosure are not necessarily limited to the effects described here, but may include any of the effects described herein.

BRIEF DESCRIPTION OF DRAWING

FIG. 1 is a diagram illustrating a planar configuration example of a biological information measurement device according to a first embodiment of the present disclosure.

FIG. 2 is a diagram illustrating a cross-sectional configuration example of the biological information measurement device in FIG. 1.

FIG. 3 is a diagram illustrating an application example of the biological information measurement device in FIG. 1.

FIG. 4 is a diagram illustrating a side configuration example of a wearable apparatus in FIG. 3.

FIG. 5 is a diagram illustrating a functional block example of the biological information measurement device in FIG. 1.

FIG. 6 is a diagram illustrating a configuration example of a switching unit in FIG. 5.

FIG. 7 is a diagram illustrating a functional block example of a processing section in FIG. 3.

FIG. 8 is a diagram illustrating an example of a procedure of attribute discrimination by the biological information measurement device in FIG. 1.

FIG. 9 is a diagram illustrating an example of a procedure of electrode switching by the biological information measurement device in FIG. 1.

FIG. 10A is a diagram illustrating an example of a detection signal obtained when all electrodes are connected. FIG. 10B is a diagram illustrating an example of a detection signal obtained after a portion of electrodes is disconnected.

FIG. 11A is a diagram illustrating an example of detection data obtained at time of measurement per electrode pair. FIG. 11B is a diagram illustrating an example of a detection signal obtained when all the electrodes are connected.

FIG. 12 is a diagram illustrating an example of a procedure of periodic measurement by the biological information measurement device in FIG. 1.

FIG. 13 is a diagram illustrating an example of a procedure of noise reduction by the biological information measurement device in FIG. 1.

FIG. 14 is a diagram illustrating that noise is reduced by the biological information measurement device in FIG. 1.

FIG. 15 is a diagram illustrating an example of a planar configuration of a biological information measurement device according to a second embodiment of the present disclosure.

FIG. 16 is a diagram illustrating a cross-sectional configuration example of the biological information measurement device in FIG. 15.

FIG. 17 is a diagram illustrating an application example of the biological information measurement device in FIG. 15.

FIG. 18 is a diagram illustrating a side configuration example of a wearable apparatus in FIG. 17.

FIG. 19 is a diagram illustrating a functional block example of the biological information measurement device in FIG. 15.

FIG. 20 is a diagram illustrating an example of a procedure of each type of analysis by the biological information measurement device in FIG. 15.

FIG. 21 is a diagram illustrating a modification example of the biological information measurement device in FIG. 15.

FIG. 22 is a diagram illustrating a cross-sectional configuration example of the biological information measurement device in FIG. 21.

FIG. 23 is a diagram illustrating an application example of the biological information measurement device in FIG. 21.

FIG. 24 is a diagram illustrating a functional block example of the biological information measurement device in FIG. 21.

FIG. 25 is a diagram illustrating an example of a procedure of periodic measurement by the biological information measurement device in FIG. 21.

FIG. 26 is a diagram illustrating a planar configuration example of a biological information measurement device according to a third embodiment of the present disclosure.

FIG. 27 is a diagram illustrating a cross-sectional configuration example of the biological information measurement device in FIG. 26.

FIG. 28 is a diagram illustrating an application example of the biological information measurement device in FIG. 26.

FIG. 29 is a diagram illustrating a side configuration example of a wearable apparatus in FIG. 28.

FIG. 30 is a diagram illustrating a functional block example of the biological information measurement device in FIG. 26.

FIG. 31 is a diagram illustrating a modification example of a functional block of the biological information measurement device in FIG. 15.

FIG. 32 is a diagram illustrating a modification example of a functional block of the biological information measurement device in FIG. 26.

FIG. 33 is a diagram illustrating an example in which a wearable apparatus including the biological information measurement device in each of FIGS. 1, 15, and 26 and a terminal apparatus are coupled via a network.

FIG. 34 is a diagram illustrating an example in which a wearable apparatus including the biological information measurement device in each of FIG. 1 and a terminal apparatus are coupled via a network.

FIG. 35 is a diagram illustrating an example in which a wearable apparatus including the biological information measurement device in each of FIG. 15 and a terminal apparatus are coupled via a network.

FIG. 36 is a diagram illustrating an example in which a wearable apparatus including the biological information measurement device in each of FIG. 26 and a terminal apparatus are coupled via a network.

FIG. 37 is a diagram illustrating an example of a functional block of the terminal apparatus in each of FIGS. 33 to 36.

MODES FOR CARRYING OUT THE INVENTION

Hereinafter, embodiments for practicing the present disclosure are described in detail with reference to the drawings. It is to be noted that description is given in the following order.
1. First Embodiment (Biological Information Measurement Device) . . . FIGS. 1, 2, 3, 4, 5, 6, 7, 8, 9, 10A, 10B, 11A, 11B, 12, 13, and 14
   Example in Which Attribute Determination, Electrode Switching, and Noise Reduction Are Performed
2. Second Embodiment (Biological Information Measurement Device) . . . FIGS. 15 to 20 Example in Which Contact Analysis, Body Motion Analysis, and Pressure Analysis Are Performed
3. Modification Example of Second Embodiment (Biological Information Measurement Device) . . . FIGS. 21 to 25 Example in Which There Is Provided Plurality of Electrode Pairs
4. Third Embodiment (Biological Information Measurement Device) . . . FIGS. 26 to 30 Example in Which First Embodiment and Second Embodiment Are Combined
5. Another Modification Example of Second Embodiment (Biological Information Measurement Device) . . . FIGS. 31 and 32 Example in Which Learning Data Are Used
6. Application Example of Each Embodiment (Biological Information Measurement System) . . . FIGS. 33 to 37
   Example in Which Biological Information Measurement Device and Terminal Apparatus Communicate with Each Other via Network 1. First Embodiment Humans each have a function of sweating on the body surface as a response of the autonomous nervous system to a change in the environment. Sweating includes thermal sweating for adjusting the body temperature in a hot environment or during exercise, mental sweating observed when receiving a mental stimulus such as mental tension or emotional change, gustatory sweating observed, for example, when eating something hot and spicy, or the like.

There is biological measurement called sweating measurement that acquires a change brought about by this sweating on the body surface. Sweating measurement is performed by using a sweat sensor. It is a general technique in sweating measurement to dispose at least two or more electrodes on the body surface, apply a voltage or cause a current to flow between the electrodes, and acquire a change in impedance (or a change in conductance) between the electrodes. The change is brought about by sweating on the body surface.

In sweating measurement, the active sweat glands or the amount of sweat on the current path influences a measurement result. In daily use, a wrist on which a wristwatch or the like is worn is supposed to be useful as a measurement site. Wrists, however, have less active sweat glands and less changes in the amount of sweat than fingers and palms. In addition, active sweat glands vary in distribution among individuals, and it is not possible to identify the place thereof. This makes it difficult to measure a skin conductance response for detecting mental sweating.

Methods of solving this include a method of increasing the area of electrodes and the detection rate of active sweat glands to increase signal intensity for detection. However, such a method also leads to more regions subjected to changes in contact between electrodes and skin. Depending on the state of a worn sweat sensor, a change in contact between an electrode and skin is more likely to generate noise. In a case where there is a change in contact between an electrode and skin, conductance caused by a change in a resistance component and a capacity component present at that position changes and appears as noise. The present disclosure focuses on this principle of a change in a resistance component and a capacity component, and proposes a technique of removing a noise source between an electrode and skin or reducing noise caused by a change in pressure of contact by using data measured by the individual electrode pairs and data measured with the respective electrode pairs integrated.

[Configuration]

FIG. 1 illustrates an example of a planar configuration of a biological information measurement device 1 according to a first embodiment of the present disclosure. FIG. 2 illustrates an example of a cross-sectional configuration of the biological information measurement device 1 in FIG. 1. FIG. 3 illustrates an application example of the biological information measurement device 1 in FIG. 1. FIG. 3 illustrates, as an example, that the biological information measurement device 1 is built in a wristband-type or wristwatch-type wearable apparatus 100. FIG. 4 illustrates an example of a side configuration of the wearable apparatus 100 in FIG. 3. FIG. 5 illustrates an example of a functional block of the biological information measurement device 1.

The biological information measurement device 1 is a device that measures mental sweating by measuring a skin impedance change (or a skin conductance change) that is a kind of biological information of a subject 200. The biological information measurement device 1 includes, for example, a wiring board 10A and a plurality of electrode pairs 11, 12, 13, and 14 formed on the wiring board 10A. The wiring board 10A supports the plurality of electrode pairs 11, 12, 13, and 14, and electrically couples the respective electrode pairs 11, 12, 13, and 14 and a wiring board 10B described below. The respective electrode pairs 11, 12, 13, and 14 are brought into contact with skin, and used to detect changes in impedance or conductance between the electrodes of the electrode pairs.

The wiring board 10A is obtained, for example, by forming a wiring layer on a resin substrate or a resin film. The electrode pair 11 includes two electrodes 11A and 11B that are, for example, spaced apart and disposed on the surface of the wiring board 10A to be opposed to each other. The electrode pair 12 includes two electrodes 12A and 12B that are, for example, spaced apart and disposed on the surface of the wiring board 10A to be opposed to each other. The electrode pair 13 includes two electrodes 13A and 13B that are, for example, spaced apart and disposed on the surface of the wiring board 10A to be opposed to each other. The electrode pair 14 includes two electrodes 14A and 14B that are, for example, spaced apart and disposed on the surface of the wiring board 10A to be opposed to each other. Each of the electrode pairs 11, 12, 13, and 14 includes, for example, a metallic material such as silver or stainless steel.

The biological information measurement device 1 further includes, for example, the wiring board 10B, a switching unit 15, an analog unit 16, a signal processing unit 17, and a communication unit 18. The wiring board 10B is formed as a different entity from the wiring board 10A. The switching unit 15, the analog unit 16, the signal processing unit 17, and the communication unit 18 are formed on the wiring board 10B. The wiring board 10B supports the switching unit 15, the analog unit 16, the signal processing unit 17, and the communication unit 18, and electrically couples the switching unit 15, the analog unit 16, the signal processing unit 17, and the communication unit 18, and the respective electrode pairs 11, 12, 13, and 14.

The switching unit 15 connects and disconnects (first connection and disconnection) the electrodes 11A, 12A, 13A, and 14A that are ones of the electrodes of the respective electrode pairs 11, 12, 13, and 14 and a power supply section 16D described below, and connects and disconnects (second connection and disconnection) the electrodes 11B, 12B, 13B, and 14B that are the others of the electrodes of the respective electrode pairs 11, 12, 13, and 14 and an IV conversion section 16A (or an AD (Analog-to-Digital) conversion section 17A) described below. The analog unit 16 performs predetermined signal processing on an analog detection signal SG obtained from the connection and disconnection by the switching unit 15. The signal processing unit 17, for example, controls the power supply section 16D and the switching unit 15, digitalizes the detection signal SG inputted from the analog unit 16, and performs predetermined signal processing on the digitalized detection signal SG. The communication unit 18 transmits a noise-reduced signal SGc generated from the predetermined signal processing by the signal processing unit 17 to an external apparatus (e.g., terminal apparatus 600 described below). The wiring board 10A and the wiring board 10B are electrically coupled to each other, for example, via FPC (Flexible printed circuits) or the like.

The biological information measurement device 1 is built in the wristband-type or wristwatch-type wearable apparatus 100, for example. The wearable apparatus 100 then includes, for example, a housing 20 and a wrist fixation belt 21. The wiring board 10B, and the switching unit 15, the analog unit 16, the signal processing unit 17, and the communication unit 18 on the wiring board 10B are housed in the housing 20. The wrist fixation belt 21 supports the wiring board 10A to bring the respective electrode pairs 11, 12, 13, and 14 into contact with the skin of the wrist.

(Switching Unit 15)

FIG. 6 illustrates an example of a configuration of the switching unit 15. The switching unit 15 includes, for example, an n-input/n-output multiplexer. The switching unit 15 includes, for example, a switching section 15A that connects and disconnects (first connection and disconnection) the electrodes 11A, 12A, 13A, and 14A that are ones of the electrodes of the respective electrode pairs 11, 12, 13, and 14 and the power supply section 16D, and a switching section 15B that connects and disconnects (second connection and disconnection) the electrodes 11B, 12B, 13B, and 14B that are the others of the electrodes of the respective electrode pairs 11, 12, 13, and 14 and the IV conversion section 16A (or the paths leading to the AD (Analog-to-Digital) conversion section 17A described below) described below.

The switching section 15A includes, for example, a switch SW1, a switch SW2, a switch SW3, and a switch SW4. The switch SW1 connects and disconnects the electrode 11A and the power supply section 16D. The switch SW2 connects and disconnects the electrode 12A and the power supply section 16D. The switch SW3 connects and disconnects the electrode 13A and the power supply section 16D. The switch SW4 connects and disconnects the electrode 14A and the power supply section 16D. The switching section 15A connects and disconnects (first connection and disconnection) the electrodes 11A, 12A, 13A, and 14A and the power supply section 16D, for example, on the basis of control signals Crl (Crl1) from a control section 17D described below.

The switching section 15B includes, for example, a switch SW5, a switch SW6, a switch SW7, and a switch SW8. The switch SW5 connects and disconnects the electrode 11B and the IV conversion section 16A (or a path leading to the AD conversion section 17A). The switch SW6 connects and disconnects the electrode 12B and the IV conversion section 16A (or a path leading to the AD conversion section 17A). The switch SW7 connects and disconnects the electrode 13B and the IV conversion section 16A (or a path leading to the AD conversion section 17A). The switch SW8 connects and disconnects the electrode 14B and the IV conversion section 16A (or a path leading to the AD conversion section 17A). The switching section 15B connects and disconnects (second connection and disconnection) the electrodes 11B, 12B, 13B, and 14B and the IV conversion section 16A (or the paths leading to the AD conversion section 17A), for example, on the basis of control signals Crl (Crl2) from the control section 17D described below.

For example, in a case where the control signals Crl from the control section 17D are signals for instructing SW1 and SW5 to turn on, the switching unit 15 inputs a current outputted from the power supply section 16D to the IV conversion section 16A (or the path leading to the AD conversion section 17A) via SW1, 11A, 11B, and SW5 by turning on SW1 and SW5. The following refers to an analog detection signal SG outputted at this time from the switching section 15B to the IV conversion section 16A as detection signal SG1. In addition, the measurement at this time is referred to as "single electrode pair measurement". In addition, for example, in a case where the control signals Crl from the control section 17D are signals for instructing SW2 and SW6 to turn on, the switching unit 15 inputs a current outputted from the power supply section 16D to the IV conversion section 16A (or the path leading to the AD conversion section 17A) via SW2, 12A, 12B, and SW6 by turning on SW2 and SW6. The following refers to an analog detection signal SG outputted at this time from the switching section 15B to the IV conversion section 16A as detection signal SG2. In addition, the measurement at this time is referred to as "single electrode pair measurement".

In addition, for example, in a case where the control signals Crl from the control section 17D are signals for instructing SW3 and SW7 to turn on, the switching unit 15 inputs a current outputted from the power supply section 16D to the IV conversion section 16A (or the path leading to the AD conversion section 17A) via SW3, 13A, 13B, and SW7 by turning on SW3 and SW7. The following refers to an analog detection signal SG outputted at this time from the switching section 15B to the IV conversion section 16A as detection signal SG3. In addition, the measurement at this time is referred to as "single electrode pair measurement". In addition, for example, in a case where the control signals Crl from the control section 17D are signals for instructing SW4 and SW8 to turn on, the switching unit 15 inputs a current outputted from the power supply section 16D to the IV conversion section 16A (or the path leading to the AD conversion section 17A) via SW4, 14A, 14B, and SW8 by turning on SW4 and SW8. The following refers to an analog detection signal SG outputted at this time from the switching section 15B to the IV conversion section 16A as detection signal SG4. In addition, the measurement at this time is referred to as "single electrode pair measurement".

In addition, for example, in a case where the control signals Crl from the control section 17D are signals for instructing all SW1 to SW8 to turn on, the switching unit 15 inputs a current outputted from the power supply section 16D to the IV conversion section 16A (or the paths leading to the AD conversion section 17A) via SW1 to SW4, 11 to 14, and SW5 to 8 by turning on all SW1 to SW8. The following refers to an analog detection signal SG outputted at this time from the switching section 15B to the IV conversion section 16A as detection signal SGall. In addition, the measurement at this time is referred to as "integrated electrode pair measurement".

(Analog Unit 16)

The analog unit 16 includes, for example, the IV conversion section 16A, an amplification section 16B, a filter section 16C, and the power supply section 16D. The IV conversion section 16A converts a current signal inputted from the switching unit 15 into a voltage signal. The amplification section 16B amplifies the voltage signal inputted from the IV conversion section 16A. The filter section 16C reduces an unnecessary frequency component included in the voltage signal inputted from the amplification section 16B, and extracts a fluctuation component of the voltage signal. The power supply section 16D applies predetermined voltages or currents to the electrodes 11A, 12A, 13A, and 14A via the switching unit 15 at predetermined timing under the control of the control section 17D.

(Signal Processing Unit 17)

The signal processing unit 17 includes, for example, the AD conversion section 17A, a storage section 17B, a processing section 17C, and the control section 17D. The AD conversion section 17A converts an analog signal inputted from the analog unit 16 into a digital signal. The storage section 17B stores the digital signal outputted from the AD conversion section 17A. The storage section 17B includes, for example, a nonvolatile memory, and includes, for example, EEPROM (Electrically Erasable Programmable Read-Only Memory), a flash memory, a resistive random access memory, or the like.

The processing section 17C executes the contents executed by each functional block illustrated in FIG. 7. The control section 17D controls the application of voltages or currents from the power supply section 16D to the electrodes 11A, 12A, 13A, and 14A. The control section 17D further controls the above-described first connection and disconnection and the above-described second connection and disconnection by the switching unit 15. The control section 17D controls the above-described first connection and disconnection by the switching unit 15 and the above-described second connection and disconnection by the switching unit 15, thereby inputting, to the AD conversion section 17A, a plurality of analog signals (first analog signals) for changes in impedance or conductance between the electrodes of the individual electrode pairs 11, 12, 13, and 14 and an analog signal (second analog signal) for a change in impedance or conductance between the electrodes of the plurality of electrode pairs 11, 12, 13, and 14.

FIG. 7 illustrates an example of a functional block of the processing section 17C. The processing section 17C includes, for example, a data acquisition section 171, a saturation determination section 172, an electrode configuration setting section 173, and a noise reduction processing section 174. The data acquisition section 171 reads out the detection signal SG and attribute data Dpr from the storage section 17B. The data acquisition section 171 outputs the read detection signal SG to the saturation determination section 172 and the noise reduction processing section 174. The saturation determination section 172 executes the attribute discrimination illustrated in FIG. 8. The electrode configuration setting section 173 executes the electrode setting in electrode switching that is illustrated in FIG. 9. The electrode configuration setting section 173 further executes the electrode setting in periodic measurement that is illustrated in FIG. 12. The noise reduction processing section 174 executes the noise reduction illustrated in FIG. 13.

(Attribute Discrimination)

FIG. 8 illustrates an example of a procedure of attribute discrimination. The processing section 17C (saturation determination section 172) first reads out the detection signal SG from the storage section 17B (step S101). Next, the processing section 17C determines whether or not the detection signal SG is saturated (step S102). The saturation refers to the saturation of the measuring range of the AD conversion section 17A. The saturation includes a state (high saturated) in which an electrode pair is short-circuited to cause conductance to exceed the measuring range and get too high, and a state (low saturated) in which an electrode pair does not come into contact with skin to cause conductance to fall below the measuring range and get too low. In a case where a result of the determination indicates that the detection signal SG is unsaturated (neither the high saturated state nor the low saturated state), the processing section 17C imparts an "unsaturated" attribute to the detection signal SG (step S103).

In a case where the plurality of detection signals SG includes a signal generated by the input of a signal that saturates the measuring range of the AD conversion section 17A, the processing section 17C determines whether or not the detection signal SG is in high saturated or low saturated (step S104). In a case where a result thereof indicates that the detection signal SG is in high saturated, the processing section 17C imparts a "high saturated" attribute to the detection signal SG (step S105). In contrast, in a case where the detection signal SG is in low saturated, the processing section 17C imparts a "low saturated" attribute to the detection signal SG (step S106). Afterwards, the processing section 17C associates the imparted attribute with the detection signal SG to create the attribute data Dpr, and stores the attribute data Dpr in the storage section 17B (step S107).

(Electrode Switching)

FIG. 9 illustrates an example of a procedure of electrode switching. The processing section 17C (electrode configuration setting section 173) first reads out the attribute data Dpr from the storage section 17B (step S201). Next, the processing section 17C discriminates a measurement type (step S202). The processing section 17C reads out data for measurement types, for example, from the storage section 17B, and discriminates a measurement type on the basis of the read data.

The storage section 17B stores data corresponding to "integrated electrode pair measurement" as the initial value of the data for measurement types. At first, the data for measurement types are thus the data corresponding to the "integrated electrode pair measurement". Accordingly, the processing section 17C outputs control signals to the switching unit 15 via the control section 17D. The control signals instruct that all electrode pairs to be coupled be coupled. The electrode pairs to be coupled are decided on the basis of the attribute data Dpr. The processing section 17C outputs, to the switching unit 15 via the control section 17D, control signals that, for example, instruct all the electrode pairs (e.g., all the electrode pairs 11, 12, 13, and 14) to be coupled for which the detection signals SG to which the "unsaturated" attributes are imparted are obtained. As a result, the electrode pairs are coupled on the basis of the attribute data Dpr (step S203). Next, the processing section 17C stores the detection signal SGall in the storage section 17B (step S204). The detection signal SGall is obtained via the electrode pairs coupled on the basis of the attribute data Dpr. Afterwards, the processing section 17C stores the data corresponding to the "single electrode pair measurement" in the storage section 17B as the data for measurement types. As a result, the data for measurement types is changed into the data corresponding to the "single electrode pair measurement" (step S205).

The processing section 17C discriminates a measurement type again (step S202). The processing section 17C reads out data for measurement types, for example, from the storage section 17B, and discriminates a measurement type on the basis of the read data.

The storage section 17B then stores data corresponding to "single electrode pair measurement" as the data for measurement types. Accordingly, the processing section 17C outputs control signals to the switching unit 15 via the control section 17D. The control signals instruct that electrode pairs to be individually coupled be coupled. The electrode pairs to be coupled are decided on the basis of the attribute data Dpr. The signal processing unit 17 outputs, to the switching unit 15 via the control section 17D, control signals that, for example, instruct all the electrode pairs (e.g., all the electrode pairs 11, 12, 13, and 14) to be coupled for which the detection signals SG to which the "unsaturated" attributes are imparted are obtained. As a result, the electrode pairs are sequentially coupled on the basis of the attribute data Dpr (step S206). Next, the processing section 17C stores the detection signal SGk in the storage section 17B (step S207). The detection signal SGk is obtained via the electrode pairs coupled on the basis of the attribute data Dpr. Next, the processing section 17C determines whether or not measurement by all the electrode pairs to be coupled is finished (step S208). In a case where a result thereof indicates that measurement by all the electrode pairs to be coupled is not finished, the processing section 17C outputs a control signal to the switching unit 15 via the control section 17D (step S209). The control signal instructs another electrode pair to be coupled on the basis of the attribute data Dpr. Afterwards, the processing section 17C repeatedly executes steps S207, S208, and S209. When measurement by all the electrode pairs to be coupled is finished, the processing section 17C terminates the electrode switching.

FIG. 10A illustrates an example of the detection signal SGall obtained when all the electrode pairs 11, 12, 13, and 14 are connected. FIG. 10B illustrates an example of the detection signal SGall obtained after a portion (e.g., electrode pairs 12 and 13) of the electrode pairs are disconnected. FIGS. 10A and 10B each exemplify a case where the electrode pairs 12 and 13 are not in contact with skin, and stay in a low conductance state (i.e., low saturated state). While FIG. 10A illustrates that the detection signal SGall has noise, FIG. 10B illustrates that the detection signal SGall has no noise. This indicates that disconnecting electrode pairs in the low saturated state allows the noise of the detection signal SGall to be reduced.

FIG. 11A illustrates an example of the detection signal SGk obtained from measurement by each of the electrode pairs 11, 12, 13, and 14. FIG. 11B illustrates an example of the detection signal SGall obtained when all the electrode pairs 11, 12, 13, and 14 are connected. FIG. 11A illustrates that the electrode pairs 12 and 13 each have a change in pressure of contact, and the detection signals SG2 and SG3 thus have noise. FIG. 11B illustrates that the profile of the noise of the detection signal SGall is the same as the profile of the noise of the detection signals SG2 and SG3 in FIG. 11A.

(Periodic Measurement)

FIG. 12 illustrates an example of a procedure of periodic measurement. The processing section 17C first determines whether or not there is an instruction to start measurement (step S301). The signal processing unit 17 issues an instruction to start measurement, for example, when a predetermined time elapses, a user makes a request, or a user does exercise. In a case where a result thereof indicates that there is an instruction to start measurement, the signal processing unit 17 instructs the power supply section 16D to apply a voltage/current to an electrode pair (step S302). Afterwards, the signal processing unit 17 waits for a predetermined time (step S303), and then determines whether or not a sampling period is reached (step S304). In a case where a result thereof indicates that the waiting time reaches the sampling period, the signal processing unit 17 generates the attribute data Dpr while switching electrode pairs, stores the attribute data Dpr in the storage section 17B, acquires the detection signal SG, and stores the in detection signal SG in the storage section 17B (steps S305, S101 to S107, and S201 to S209). Afterwards, the signal processing unit 17 determines whether or not there is an instruction to terminate the measurement (step S306). In a case where a result thereof indicates that there is an instruction to terminate the measurement, the signal processing unit 17 instructs the power supply section 16D to stop applying a voltage/current to an electrode pair (step S307). In a case where there is no instruction to terminate the measurement, the signal processing unit 17 executes step S305 whenever the waiting time reaches the sampling period.

(Noise Reduction)

FIG. 13 illustrates an example of a procedure of noise reduction. The processing section 17C (noise reduction processing section 174) reads out the detection signals SGall and SGk from the storage section 17B (step S401). Next, the processing section 17C selects one or more detection signals SGk including more noise among the plurality of read detection signals SGk as detection signals SGz (step S402). In a case where the plurality of read detection signals SGk includes a plurality of signals having more noise, a signal obtained by adding together the plurality of detection signals SGk having more noise is treated as the detection signal SGz.

Incidentally, the amount of noise is obtained by finding a difference between the waveform of the detection signal SGk and a waveform obtained by approximating the waveform of the detection signal SGk, for example, with an approximation expression as in the following Expression 1. τ1 and τ2 represent time constants. C represents a correction coefficient.

$$C\left(e^{-\frac{1}{\tau 1}} - e^{-\frac{1}{\tau 2}}\right) \qquad \text{[Equation 1]}$$

The processing section 17C derives a noise-reduced signal SGc on the basis of the plurality of detection signals SGk (first digital signals) and the detection signal SGall (second digital signal). The plurality of detection signals SGk (first digital signals) is obtained by converting the plurality of first analog signals by the AD conversion section 17A. The detection signal SGall (second digital signal) is obtained by converting the second analog signal by the AD conversion section 17A. In the noise-reduced signal SGc, the noise included in the detection signal SGall (second digital signal) is reduced. Specifically, the processing section 17C subtracts the one or more selected detection signals SGk (=detection signals SGz) from the detection signal SGall to derive the noise-reduced signal SGc (step S403). The processing section 17C outputs the derived noise-reduced signal SGc to the external apparatus (e.g., terminal apparatus 600) via the communication unit 18.

FIG. 14 schematically illustrates a procedure of noise removal. FIG. 14 exemplifies the detection signals SG2 and SG3 as the detection signals SGk including more noise. The processing section 17C (noise reduction processing section 174) removes the detection signals SG2 and SG3 including more noise from the detection signal SGall read out from the storage section 17B to obtain the noise-reduced signal SGc in which noise is reduced.

[Effects]

Next, the effects of the biological information measurement device 1 are described.

The invention described in Japanese Unexamined Patent Application Publication (Published Japanese Translation of PCT Application) No. JP 2015-520656 (that is referred to as "prior art A" below) has an object to make it possible to measure and collect a skin conductance level (SCL) or skin conductance response (SCR) of an individual. The contents of the prior art A are to dispose a plurality of electrode pairs for a handheld device, and activate and bundle up only the electrodes at a portion grasped by a hand of a human to measure one skin conductance response.

The prior art A has a configuration similar to that of the present embodiment in that a plurality of electrodes is bundled up. It is not, however, possible for the prior art A to address noise superimposed by a change in pressure of contact of electrodes. Different from a condition for use in only a specific scene like handheld devices, devices worn on wrists are supposed to be constantly used. In this case, due to a finger motion and a twisted wrist, a change in pressure of contact between electrodes and skin that is brought about by the deformed wrist is superimposed as noise, leaving a practical problem.

The invention described in Japanese Unexamined Patent Application Publication (Published Japanese Translation of PCT Application) No. JP 2016-516461 (that is referred to as "prior art B" below) has an object to provide a novel system or the like that allows skin conductance to be measured with high reliability and repeatability without suffering from electrolysis. The prior art B disposes two types of electrodes including a first electrode and a second electrode, applies biases of V+ and V− to the respective electrodes, measures a current flowing between the first electrode and the second electrode, and provides a mechanism that adjusts a first voltage, a second voltage, a compensation current, or the like. This prevents an output voltage at the time of measurement from being unsaturated.

In the prior art B, a skin conductance value sometimes saturates the measuring range when finally inputted to an AD converter. To eliminate such saturation in the prior art B, it is necessary to change the value of a voltage provided to a target to be measured. However, in such a case, the output of a living tissue or a skin conductance response to be measured may be influenced. In addition, in a case of high saturated, there is a possibility that electrodes are short-circuited. In a case of low saturated, there is a possibility that a foreign substance is sandwiched. This requires a technique of avoiding being unsaturated without changing an applied voltage.

The invention described in Japanese Unexamined Patent Application Publication No. 2014-23711 (that is referred to as "Patent Literature C" below) has an object to reduce the influence of polarization generated when practical electrodes are used without limiting the frequency of an applied voltage or increasing the circuit scale or the number of parts. The Patent Literature C provides two types of electrodes including a first electrode and a second electrode, and also provides a plurality of switches for polarity switching to configure a first signal path and a second signal path. In the first signal path, signals flow in the order of the first electrode and the second electrode. In the second signal path, signals flow in reverse order. The Patent Literature C performs an operation of switching the respective signal paths in a predetermined period to reduce the influence of a polarization voltage generated between the electrodes and a target to be measured.

To reduce the influence of polarization, polarity switching is general. This technique is limited to two types of electrodes including a first electrode and a second electrode. Accordingly, if a general user, for example, has a foreign substance sandwiched between one of the electrodes and the skin when using a device equipped with the technique, conductance measurement is not established.

In contrast, the biological information measurement device 1 according to the present embodiment derives the noise-reduced signal SGc on the basis of a plurality of detection signals (first analog signals) for changes in impedance or conductance between the electrodes of the individual electrode pairs 11, 12, 13, and 14 and a detection signal (second analog signal) for a change in impedance or conductance between the electrodes of the plurality of electrode pairs 11, 12, 13, and 14. In the noise-reduced signal SGc, the noise included in a digital signal (detection signal SGall (second digital signal)) is reduced. The digital signal (detection signal SGall (second digital signal)) is obtained by converting the second analog signal by the AD conversion section 17A. This reduces noise without using a noise reference obtained from another sensor. The noise is caused by changes in pressure of contact between the electrodes and the skin. As a result, it is possible to decrease the noise included in biological information (detection signal SGall).

In addition, in the present embodiment, one or more detection signals SGk (=detection signals SGz) including more noise among the plurality of detection signals SGk are selected. Further, the selected detection signals SGz are subtracted from the detection signal S Gall to derive the noise-reduced signal SGc. This reduces noise without using a noise reference obtained from another sensor. The noise is caused by changes in pressure of contact between the electrodes and the skin. As a result, it is possible to decrease the noise included in biological information (detection signal S Gall).

In addition, in the present embodiment, in a case where the plurality of detection signals SGk (first digital signals) includes a signal generated by the input of a signal that saturates the measuring range of the AD conversion section 17A, the noise-reduced signal SGc is derived on the basis of the one or more detection signals SGk (first digital signals) that do not correspond the signal and the detection signal S Gall (second digital signal). This reduces noise without using a noise reference obtained from another sensor. The noise is caused by changes in pressure of contact between the electrodes and the skin. As a result, it is possible to decrease the noise included in biological information (detection signal SGall).

In addition, in the present embodiment, control signals are inputted to the switching unit 15, thereby controlling the above-described first connection and disconnection and the above-described second connection and disconnection by the switching unit 15. This reduces noise without using a noise reference obtained from another sensor. The noise is caused by changes in pressure of contact between the electrodes and the skin. As a result, it is possible to decrease the noise included in biological information (detection signal S Gall).

In addition, in the present embodiment, the wrist fixation belt 21 is provided that supports the wiring board 10A to bring the respective electrode pairs 11, 12, 13, and 14 into contact with the skin of the wrist. This reduces noise caused by changes in pressure of contact between the electrodes and the skin, making it possible to decrease the noise included in the biological information (detection signal S Gall).

2. Second Embodiment

Next, a biological information measurement device 2 according to a second embodiment of the present disclosure is described. FIG. 15 illustrates an example of a planar configuration of the biological information measurement device 2. FIG. 16 illustrates an example of a cross-sectional configuration of the biological information measurement device 2. FIG. 17 illustrates an application example of the biological information measurement device 2. FIG. 17 illustrates, as an example, that the biological information measurement device 2 is built in a wristband-type or wristwatch-type wearable apparatus 300. FIG. 18 illustrates an example of a side configuration of the wearable apparatus 300. FIG. 19 illustrates an example of a functional block of the biological information measurement device 2.

The biological information measurement device 2 is a device that measures mental sweating by measuring a skin impedance change (or a skin conductance change) that is a kind of biological information of the subject 200. The biological information measurement device 2 includes, for example, the wiring board 10A, the electrode pair 11, and two pressure sensors 22. The electrode pair 11 is formed on the wiring board 10A. The two pressure sensors 22 detect a state of pressure. The wiring board 10A supports the electrode pair 11, and electrically couples the electrode pair 11 and the wiring board 10B. The electrode pair 11 is brought into contact with skin, and used to detect a change in impedance or conductance between the electrodes of the electrode pair. Each pressure sensor 22 detects the pressure of the electrode pair 11 on the skin, and is disposed, for example, between the electrode pair 11 and the wiring board 10A.

The biological information measurement device 2 further includes, for example, the wiring board 10B, an acceleration sensor 23, an analog unit 24, a signal processing unit 25, and the communication unit 18. The wiring board 10B is formed as a different entity from the wiring board 10A. The acceleration sensor 23, the analog unit 24, the signal processing unit 25, and the communication unit 18 are formed on the wiring board 10A. The wiring board 10B supports the acceleration sensor 23, the analog unit 24, the signal processing unit 25, and the communication unit 18, and electrically couples the acceleration sensor 23, the analog unit 24, the signal processing unit 25, and the communication unit 18, and the electrode pair 11.

The analog unit 24 performs predetermined signal processing on the analog detection signal SG obtained from the electrode pair 11. The signal processing unit 25, for example, controls the power supply section 16D, digitalizes the detection signal SG inputted from the analog unit 24, and performs predetermined signal processing on the digitalized detection signal SG. The communication unit 18 transmits one or more detection signals SG (biological signals having less noise) having a reliability degree 1 to the external apparatus (e.g., terminal apparatus 600 described below). The one or more detection signals SG are obtained as a result of the determination by the signal processing unit 25. The wiring board 10A and the wiring board 10B are electrically coupled to each other, for example, via FPC or the like.

The biological information measurement device 2 is built in the wristband-type or wristwatch-type wearable apparatus 300, for example. The wearable apparatus 300 then includes, for example, the housing 20 and the wrist fixation belt 21. The wiring board 10B, and the acceleration sensor 23, the analog unit 24, the signal processing unit 25, and the communication unit 18 on the wiring board 10B are housed in the housing 20. The wrist fixation belt 21 supports the wiring board 10A to bring the electrode pair 11 into contact with the skin of the wrist.

(Analog Unit 24)

The analog unit 24 includes, for example, the IV conversion section 16A, the amplification section 16B, the filter section 16C, and the power supply section 16D. The IV conversion section 16A converts a current signal inputted from the electrode pair 11 into a voltage signal. The amplification section 16B amplifies the voltage signal inputted from the IV conversion section 16A. The filter section 16C reduces an unnecessary frequency component included in the voltage signal inputted from the amplification section 16B, and extracts a fluctuation component of the voltage signal. The power supply section 16D applies a predetermined voltage or current to the electrode 11A at predetermined timing under the control of the control section 17D.

The analog unit 24 further includes, for example, a filter section 24A1, a filter section 24A2, and a filter section 24B. The filter section 24A1 is coupled to the output of the pressure sensor 22 provided between the electrode 11A and the wiring board 10A. The filter section 24A2 is coupled to the output of the pressure sensor 22 provided between the electrode 11B and the wiring board 10A. The filter section 24B is coupled to the output of the acceleration sensor 23. The filter section 24A1 stores a detected pressure signal Dp1 in the storage section 17B. The filter section 24A2 stores a detected pressure signal Dp2 in the storage section 17B. The filter section 24B stores a detected acceleration signal Dm in the storage section 17B.

(Signal Processing Unit 25)

The signal processing unit 25 includes, for example, the AD conversion section 17A, the storage section 17B, a processing section 17C, and the control section 25A. The AD conversion section 17A converts an analog signal inputted from the analog unit 24 into a digital signal. The storage section 17B stores the digital signal outputted from the analog unit 24 (e.g., AD conversion section 17A).

The processing section 25A executes the contact analysis, body motion analysis, and pressure analysis illustrated in FIG. 20. The processing section 25A first reads out the detection signal SG from the storage section 17B (step S501). Next, the processing section 25A determines whether or not the detection signal SG is saturated (step S502). In a case where a result thereof indicates that the detection signal SG is saturated, the processing section 25A determines the reliability degree of the detection signal SG as 0 (step S503). In a case where the detection signal SG is not saturated, the processing section 25A reads out the acceleration signal Dm from the storage section 17B (step S504). Next, the processing section 25A derives acceleration norm data (norm Dm) from the acceleration signal Dm (step S505). The processing section 25A then determines whether or not the norm Dm is greater than or equal to a predetermined threshold Dth1 (step S506). In a case where a result thereof indicates that the norm Dm is greater than or equal to the predetermined threshold Dth1, the processing section 25A determines the reliability degree of the detection signal SG as 0 (step S503). In a case where the norm Dm is less than the predetermined threshold Dth1, the processing section 25A reads out the pressure signals Dp1 and Dp2 (step S507). The processing section 25A extracts maximum values Dmax1 and Dmax2 from the read pressure signals Dp1 and Dp2 (step S509). The processing section 25A then determines whether or not the extracted maximum values Dmax 1 and Dmax 2 are greater than or equal to a predetermined threshold Dth2 (step S509). In a case where a result thereof indicates that the maximum values Dmax1 and Dmax2 are greater than or equal to the predetermined threshold Dth2, the reliability degree of the detection signal SG is determined as 0 (step S503). In a case where the maximum values Dmax1 and Dmax2 are less than the predetermined threshold Dth2, the reliability degree of the detection signal SG is determined as 1 (step S510). The processing section 25A outputs one or more detection signals SG (biological signals having less noise) having the reliability degree 1 to the external apparatus (e.g., terminal apparatus 600 described below) via the communication unit 18. The one or more detection signals SG are obtained as a result of the determination.

Next, the effects of the biological information measurement device 2 according to the present embodiment are described.

In the present embodiment, the reliability of the detection signal SG is determined on the basis of reference data (detection signal SG, acceleration signal Dm, and pressure signals Dp1 and Dp2) for the state of contact of the electrode pair 11 with the skin, the body motion state of a user, and the state of pressure of the electrode pair 11 on the skin. The use of the above-described reference data thus allows biological signals (one or more detection signals SG having the reliability degree 1) to be extracted that have less noise caused by changes in pressure of contact between the electrode pair 11 and the skin. As a result, it is possible to acquire biological information (one or more detection signals SG having the reliability degree 1) having less noise.

3. Modification Example of Second Embodiment

Next, a modification example of the second embodiment is described. FIG. 21 illustrates one of planar configurations of the biological signal measurement device 2 according to the modification example of the second embodiment. FIG. 22 illustrates an example of a cross-sectional configuration of the biological signal measurement device 2 in FIG. 21. FIG. 23 illustrates an application example of the biological information measurement device 2 in FIG. 21. FIG. 23 illustrates, as an example, that the biological information measurement device 2 according to the present modification example is built in the wristband-type or wristwatch-type wearable apparatus 300. FIG. 24 illustrates an example of a functional block of the biological information measurement device 2 according to the present modification. includes, for example, the plurality of electrode pairs 11, 12, 13, and 14, and the plurality of pressure sensors 22. The plurality of electrode pairs 11, 12, 13, and 14 is formed on the wiring board 10A. The plurality of pressure sensors 22 is provided to the respective electrode pairs 11, 12, 13, and 14. The respective pressure sensors 22 are provided with the filter sections 24A1 to 24An.

(Periodic Measurement)

FIG. 25 illustrates an example of a procedure of periodic measurement. The processing section 25C first determines whether or not there is an instruction to start measurement (step S301). In a case where a result thereof indicates that there is an instruction to start measurement, the processing section 25A instructs the power supply section 16D to apply a voltage/current to an electrode pair (step S302). Afterwards, the processing section 25A waits for a predetermined time (step S303), and then determines whether or not a sampling period is reached (step S304). In a case where a result thereof indicates that the waiting time reaches the sampling period, the processing section 25A acquires the detection signal SG, the acceleration signal Dm, and the pressure signals Dp1 and Dp2 while switching the electrode pairs, and stores the detection signal SG, the acceleration signal Dm, and the pressure signals Dp1 and Dp2 in the storage section 17B (step S308). Afterwards, the processing section 25A executes the above-describe contact analysis, the above-described body motion analysis, and the above-described pressure analysis (steps S309 and S501 to S510). Afterwards, the processing section 25A determines whether or not there is an instruction to terminate the measurement (step S306). In a case where a result thereof indicates that there is an instruction to terminate the measurement, the processing section 25A instructs the power supply section 16D to stop applying a voltage/current to an electrode pair (step S307). In a case where there is no instruction to terminate the measurement, the processing section 25A executes step S308 whenever the waiting time reaches the sampling period.

In the present modification example, similarly to the above-described second embodiment, the reliability of the detection signal SG is determined on the basis of reference data (detection signal SG, acceleration signal Dm, and pressure signals Dp1 and Dp2) for the state of contact of the electrode pair 11 with the skin, the body motion state of a user, and the state of pressure of the electrode pair 11 on the skin. The use of the above-described reference data thus allows biological signals (one or more detection signals SG having the reliability degree 1) to be extracted that have less noise caused by changes in pressure of contact between the electrode pair 11 and the skin. As a result, it is possible to acquire biological information (one or more detection signals SG having the reliability degree 1) having less noise.

4. Third Embodiment

Next, a biological information measurement device 3 according to a third embodiment of the present disclosure is described. FIG. 26 illustrates an example of a planar configuration of the biological information measurement device 3. FIG. 27 illustrates an example of a cross-sectional configuration of the biological information measurement device 3. FIG. 28 illustrates an application example of the biological information measurement device 3. FIG. 28 illustrates, as an example, that the biological information measurement device 3 is built in a wristband-type or wristwatch-type wearable apparatus 400. FIG. 29 illustrates an example of a side configuration of the wearable apparatus 400. FIG. 30 illustrates an example of a functional block of the biological information measurement device 3.

The biological information measurement device 3 is a device that measures mental sweating by measuring a skin impedance change (or a skin conductance change) that is a kind of biological information of the subject 200. The biological information measurement device 3 includes, for example, the wiring board 10A, the plurality of electrode pairs 11, 12, 13, and 14, and the plurality of pressure sensors 22. The plurality of electrode pairs 11, 12, 13, and 14 is formed on the wiring board 10A. The plurality of pressure sensors 22 is provided to the respective electrode pairs 11, 12, 13, and 14. The wiring board 10A supports the electrode pairs 11, 12, 13, and 14, and electrically couples the electrode pairs 11, 12, 13, and 14 and the wiring board 10B.

The biological information measurement device 3 further includes, for example, the wiring board 10B, the switching unit 15, the acceleration sensor 23, the analog unit 24, a signal processing unit 31, and the communication unit 18. The wiring board 10B is formed as a different entity from the wiring board 10A. The switching unit 15, the acceleration sensor 23, the analog unit 24, the signal processing unit 31, and the communication unit 18 are formed on the wiring board 10B. The wiring board 10B supports the switching unit 15, the acceleration sensor 23, the analog unit 24, the signal processing unit 31, and the communication unit 18, and electrically couples the acceleration sensor 23, the analog unit 24, the signal processing unit 31, and the communication unit 18, and the electrode pair 11.

The analog unit 24 performs predetermined signal processing on the analog detection signals SG obtained from the electrode pairs 11, 12, 13, and 14. The signal processing unit 31, for example, controls the power supply section 16D, digitalizes the detection signals SG inputted from the analog unit 24, and performs predetermined signal processing on the digitalized detection signals SG. The communication unit 18 transmits the noise-reduced signal SGc generated from the predetermined signal processing by the signal processing unit 31 to the external apparatus (e.g., terminal apparatus 600 described below).

The biological information measurement device 3 is built in the wristband-type or wristwatch-type wearable apparatus 400, for example. The wearable apparatus 400 then includes, for example, the housing 20 and the wrist fixation belt 21. The wiring board 10B, and the acceleration sensor 23, the analog unit 24, the signal processing unit 31, and the communication unit 18 on the wiring board 10B are housed in the housing 20. The wrist fixation belt 21 supports the wiring board 10A to bring the electrode pairs 11, 12, 13, and 14 into contact with the skin of the wrist.

(Analog Unit 24)

The analog unit 24 includes, for example, the IV conversion section 16A, the amplification section 16B, the filter section 16C, and the power supply section 16D. The IV conversion section 16A converts current signals inputted from the electrode pairs 11, 12, 13, and 14 into voltage signals. The amplification section 16B amplifies the voltage signals inputted from the IV conversion section 16A. The filter section 16C reduces an unnecessary frequency component included in each voltage signal inputted from the amplification section 16B, and extracts a fluctuation component of the voltage signal. The power supply section 16D applies predetermined voltages or currents to the electrodes 11A, 12A, 13A, and 14A at predetermined timing under the control of the control section 17D.

The analog unit 24 further includes, for example, the filter sections 24A1 to 24An (n represents the number of pressure sensors 22) and the filter section 24B. The filter sections 24A1 to 24An are coupled to the outputs of the respective pressure sensors 22 provided between the electrodes 11A, 12A, 13A, and 14A, and the wiring board 10A. The filter section 24B is the output of the acceleration sensor 23. The respective filter sections 24A1 to 24An store the detected pressure signals Dp1 to Dpn in the storage section 17B. The filter section 24B stores the detected acceleration signal Dm in the storage section 17B.

(Signal Processing Unit 31)

The signal processing unit 31 includes, for example, the AD conversion section 17A, the storage section 17B, a processing section 31A, and the control section 17D. The AD conversion section 17A converts an analog signal inputted from the analog unit 24 into a digital signal. The storage section 17B stores the digital signal outputted from the analog unit 24 (e.g., AD conversion section 17A).

The processing section 31A executes the above-described contact analysis, body motion analysis, and pressure analysis (see FIG. 20). The processing section 31A further executes the above-described attribute discrimination (see FIG. 8), the above-described electrode switching (see FIG. 9), the above-described periodic measurement (see FIG. 12), and the above-described noise reduction (see FIG. 13). For example, while executing the above-described attribute discrimination (see FIG. 8), the above-described electrode switching (see FIG. 9), and the above-described periodic measurement (see FIG. 12), the processing section 31A executes the above-described contact analysis, body motion analysis, and pressure analysis (see FIG. 20). Then, the processing section 31A selects one or more detection signals SGk including more noise, for example, among the plurality of detection signals SGk determined to have the reliability degree 1 as the detection signals SGz. In a case where the plurality of detection signals SGk determined to have the reliability degree 1 includes a plurality of signals having more noise, the processing section 31A treats, for example, a signal obtained by adding together the plurality of detection signals SGk having more noise as the detection signal SGz. The processing section 31A derives the noise-reduced signal SGc, for example, on the basis of the detection signals SGz and the detection signal SGall. In the noise-reduced signal SGc, the noise included in the detection signal SGall is reduced. Specifically, the processing section 31A subtracts the one or more selected detection signals SGk (=detection signals SGz) from the detection signal SGall to derive the noise-reduced signal SGc. The processing section 31A outputs the derived noise-reduced signal SGc to the external apparatus (e.g., terminal apparatus 600) via the communication unit 18.

[Effects]

Next, the effects of the biological information measurement device 3 are described.

In the present embodiment, the reliability of the detection signal SG is determined on the basis of reference data (detection signal SG, acceleration signal Dm, and pressure signals Dp1 and Dp2) for the state of contact of the electrode pair 11 with the skin, the body motion state of a user, and the state of pressure of the electrode pair 11 on the skin. The use of the above-described reference data thus allows biological signals (one or more detection signals SG having the reliability degree 1) to be extracted that have less noise caused by changes in pressure of contact between the electrode pairs 11, 12, 13, and 14 and the skin. As a result, it is possible to acquire biological information (one or more detection signals SG having the reliability degree 1) having less noise.

In addition, in the present embodiment, one or more detection signals SGk (=detection signals SGz) including more noise among the plurality of detection signals SGk determined to have the reliability degree 1 are selected. Further, the selected detection signals SGz are subtracted from the detection signal S Gall to derive the noise-reduced signal SGc. This reduces noise without using a noise reference obtained from another sensor. The noise is caused by changes in pressure of contact between the electrodes and the skin. As a result, it is possible to decrease the noise included in biological information (detection signal SGall).

5. Modification Example Common to Second and Third Embodiments

Next, a modification example common to the second and third embodiments is described. FIG. 31 illustrates an example of a functional block of the biological signal measurement device 2 according to the modification example of the second embodiment. FIG. 32 illustrates an example of a functional block of the biological signal measurement device 3 according to the modification example of the third embodiment. In the present modification example, the pressure sensors 22, the acceleration sensor 23, and the filter sections 24A1 to 24An and 24B are omitted. Learning data DL are stored in the storage section 17B.

The learning data DL are data that are obtained through machine learning and pertain to the relationship between a biological signal (detection signal SG) and the reliability. Specifically, the learning data DL are data that are obtained on the basis of a large amount of data (detection signal SG, acceleration signal Dm, and pressure signals Dp1 and Dp2) obtained under various conditions, and pertain to the relationship between a biological signal (detection signal SG) and the reliability. The learning data DL correspond to a specific example of the "reference data" of the present disclosure.

In the present modification example, the processing sections 25A and 31A determine the reliability of a biological signal (detection signal SG) on the basis of the learning data DL. The use of the learning data DL thus allows the noise-reduced signal SGc to be extracted that has less noise caused by a change in pressure of contact between the electrode pair 11 (or the electrode pairs 11, 12, 13, and 14) and the skin. As a result, it is possible to acquire biological information (noise-reduced signal SGc) having less noise.

In addition, in the present modification example, one or more detection signals SGk (=detection signals SGz) including more noise among the plurality of detection signals SGk determined to have the reliability degree 1 are selected by the processing section 31A. Further, the processing section 31A subtracts the selected detection signals SGz from the detection signal SGall to derive the noise-reduced signal SGc. This reduces noise without using a noise reference obtained from another sensor. The noise is caused by changes in pressure of contact between the electrodes and the skin. As a result, it is possible to decrease the noise included in biological information (detection signal SGall).

6. Working Example

Next, a working example of the wearable apparatuses 100, 300, and 400 is described. FIG. 33 illustrates an application example of the wearable apparatuses 100, 300, and 400. FIG. 33 illustrates, as an example, that the wearable apparatuses 100, 300, and 400 and the terminal apparatus 600 are coupled via a network 500. The wearable apparatuses 100, 300, and 400 each transmit the noise-reduced signal SGc or biological information (one or more detection signals SG having the reliability degree 1) having less noise to the terminal apparatus 600 via the network 500. The terminal apparatus 600 performs predetermined signal processing on the basis of the received noise-reduced signal SGc or the received biological information (one or more detection signals SG having the reliability degree 1) having less noise. The terminal apparatus 600 performs a predetermined process, for example, on the signals received from wearable apparatuses 100, 300, and 400 to display the biological information on the display screen. This allows the terminal apparatus 600 to provide a user with the biological information having less noise.

It is to be noted that the wearable apparatus 100 may transmit the plurality of detected digital detection signals SG (the plurality of detection signals SGk and the detection signal S Gall) to the terminal apparatus 600 via the network 500 as illustrated in FIG. 34. In such a case, the terminal apparatus 600 performs predetermined signal processing (the above-described noise reduction process) on the basis of the plurality of received digital detection signals SG (the plurality of detection signals SGk and the detection signal SGall). The terminal apparatus 600 performs predetermined signal processing (the above-described noise reduction process), for example, on the signals received from the wearable apparatus 100 to derive the noise-reduced signal SGc and display a screen on the basis of the derived noise-reduced signal SGc. This allows the terminal apparatus 600 to provide a user with the biological information having less noise.

In addition, the wearable apparatus 300 may transmit the one or more detected digital detection signals SG, the acceleration signal Dm, and the pressure signals Dp1 to Dpn to the terminal apparatus 600 via the network 500 as illustrated in FIG. 35. In such a case, the terminal apparatus 600 performs predetermined signal processing (the above-described contact analysis, the above-described body motion analysis, and the above-described pressure analysis) on the basis of the one or more received digital detection signals SG, the acceleration signal Dm, and the pressure signals Dp1 to Dpn. The terminal apparatus 600 performs a predetermined process, for example, on the signals received from the wearable apparatus 300 to extract biological information (one or more detection signals SG having the reliability degree 1) having less noise, and display a screen on the basis of the extracted biological information (one or more detection signals SG having the reliability degree 1) having less noise. This allows the terminal apparatus 600 to provide a user with the biological information having less noise.

In addition, the wearable apparatus 400 may transmit the one or more detected digital detection signals SG, the acceleration signal Dm, and the pressure signals Dp1 to Dpn to the terminal apparatus 600 via the network 500 as illustrated in FIG. 36. In such a case, the terminal apparatus 600 performs predetermined signal processing (the above-described contact analysis, the above-described body motion analysis, and the above-described pressure analysis) on the basis of the one or more received digital detection signals SG, the acceleration signal Dm, and the pressure signals Dp1 to Dpn. The terminal apparatus 600 performs a predetermined process, for example, on the signals received from the wearable apparatus 300 to extract biological information (one or more detection signals SGk having the reliability degree 1) having less noise. The terminal apparatus 600 further performs predetermined signal processing (the above-described noise reduction process) on the basis of the one or more detection signals SGk having the reliability degree 1 and the detection signal SGall. The terminal apparatus 600 selects one or more detection signals SGk including more noise, for example, among the plurality of received detection signals SGk determined to have the reliability degree 1 as the detection signals SGk (=detection signals SGz). In a case where the plurality of detection signals SGk determined to have the reliability degree 1 includes a plurality of signals having more noise, the processing section 31A treats, for example, a signal obtained by adding together the plurality of detection signals SGk having more noise as the detection signal SGz. The terminal apparatus 600 derives the noise-reduced signal SGc, for example, on the basis of the detection signals SGz and the detection signal SGall. In the noise-reduced signal SGc, the noise included in the detection signal SGall is reduced. Specifically, the terminal apparatus 600 subtracts the detection signals SGz from the detection signal SGall to derive the noise-reduced signal SGc. The terminal apparatus 600 displays a screen on the basis of the derived noise-reduced signal SGc. This allows the terminal apparatus 600 to provide a user with the biological information having less noise.

It is to be noted that the effects described herein are merely illustrative. The effects of the present disclosure are not limited to the effects described herein. The present disclosure may have effects other than the effects described herein.

In addition, for example, it is possible to configure the present disclosure as follows.

(1)

A biological information measurement device including:

a plurality of electrode pairs that is brought into contact with skin;

a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs; and a processing section that derives a noise-reduced signal in which noise included in a second digital signal is reduced, on the basis of a plurality of first digital signals and the second digital signal, the plurality of first digital signals being obtained by converting a plurality of the first analog signals by the AD conversion section, the second digital signal being obtained by converting the second analog signal by the AD conversion section.

(2)

The biological information measurement device according to (1), in which the processing section selects the one or more first digital signals including more noise among a plurality of the first digital signals, and subtracts the one or more selected first digital signals from the second digital signal to derive the noise-reduced signal.

(3)

The biological information measurement device according to (1) or (2), in which, in a case where a plurality of the first digital signals includes a signal generated by input of a signal that saturates a measuring range of the AD conversion section, the processing section derives the noise-reduced signal on the basis of one or more first digital signals that do not correspond to the signal, and the second digital signal.

(4)

The biological information measurement device according to any one of (1) to (3), further including a connection and disconnection unit that performs the first connection and disconnection and the second connection and disconnection, in which the processing section controls the first connection and disconnection and the second connection and disconnection by the connection and disconnection unit by inputting control signals to the connection and disconnection unit.

(5)

The biological information measurement device according to any one of (1) to (4), further including:

a wiring board on which each of the electrode pairs is formed; and a wrist fixation belt that supports the wiring board to bring each of the electrode pairs into contact with skin of a wrist.

(6)

A biological information measurement system including:
a wearable apparatus; and
an external apparatus, in which
the wearable apparatus includes
a plurality of electrode pairs that is brought into contact with skin,
a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs,
a processing section that derives a noise-reduced signal in which noise included in a second digital signal is reduced, on the basis of a plurality of first digital signals and the second digital signal, the plurality of first digital signals being obtained by converting a plurality of the first analog signals by the AD conversion section, the second digital signal being obtained by converting the second analog signal by the AD conversion section, and
a transmission unit that transmits the noise-reduced signal to the external apparatus, the noise-reduced signal being derived by the processing section, and
the external apparatus includes
a reception unit that receives the noise-reduced signal from the transmission unit.

(7)

A biological information measurement system including:
a wearable apparatus; and
an external apparatus, in which
the wearable apparatus includes
a plurality of electrode pairs that is brought into contact with skin,
a control section that controls a first connection and disconnection between one of electrodes of each of the electrode pairs and a power supply section and a second connection and disconnection between another of the electrodes of each of the electrode pairs and a path leading to an AD (Analog-to-Digital) conversion section, thereby inputting, to the AD conversion section, a plurality of first analog signals for changes in impedance or conductance between the electrodes of the individual electrode pairs and a second analog signal for a change in impedance or conductance between the electrodes of a plurality of the electrode pairs, and
a transmission unit that transmits a plurality of first digital signals and a second digital signal to the external apparatus, the plurality of first digital signals being obtained by converting a plurality of the first analog signals by the AD conversion section, the second digital signal being obtained by converting the second analog signal by the AD conversion section, and
the external apparatus includes
a reception unit that receives a plurality of the first digital signals and the second digital signal from the transmission unit, and
a processing section that derives a noise-reduced signal in which noise included in the second digital signal is reduced, on the basis of a plurality of the first digital signals and the second digital signal received by the reception unit.

(8)

A biological information measurement device including:
one or more electrode pairs that are brought into contact with skin;
a power supply section that supplies the one or more electrode pairs with power;
an acquisition section that acquires one or more biological signals for changes in impedance or conductance between electrodes of the one or more electrode pairs; and
determination section that determines reliability of the one or more biological signals on the basis of reference data for a state of contact of the one or more electrode pairs with the skin, a body motion state of a user, and a state of pressure of the one or more electrode pairs on the skin, the one or more biological signals being acquired by the acquisition section.

(9)

The biological information measurement device according to (8), further including:
an acceleration sensor that detects the body motion state; and one or more pressure sensors that each detect the state of the pressure, in which the determination section acquires a first detection signal for the body motion state from the acceleration sensor and acquires second detection signals for the state of the pressure from the one or more pressure sensors as the reference data, and determines the reliability of the one or more biological signals on the basis of the acquired first detection signal and the acquired second detection signals.

(10)

The biological information measurement device according to (8) or (9), further including an AD (Analog-to-Digital) conversion section that converts the one or more biological signals into one or more digital signals, in which the determination section generates a determination result as the reference data, and determines the reliability of the one or more biological signals on the basis of the generated determination result, the determination result indicating whether or not the one or more digital signals include a signal generated by input of a signal that saturates a measuring range of the AD conversion section.

(11)

A biological information measurement system including:

a wearable apparatus; and an external apparatus, in which the wearable apparatus includes one or more electrode pairs that are brought into contact with skin, a power supply section that supplies the one or more electrode pairs with power, an acquisition section that acquires one or more biological signals for changes in impedance or conductance between electrodes of the one or more electrode pairs, a determination section that determines reliability of the one or more biological signals on the basis of reference data for a state of contact of the one or more electrode pairs with the skin, a body motion state of a user, and a state of pressure of the one or more electrode pairs on the skin, the one or more biological signals being acquired by the acquisition section, and a transmission unit that transmits a determination result of the determination section to the external apparatus, and the external apparatus includes a reception unit that receives the determination result from the transmission unit.

(12)

A biological information measurement system including:

a wearable apparatus: and an external apparatus, in which the wearable apparatus includes one or more electrode pairs that are brought into contact with skin, a power supply section that supplies the one or more electrode pairs with power, an acquisition section that acquires one or more biological signals for changes in impedance or conductance between electrodes of the one or more electrode pairs, and a transmission unit that transmits the one or more biological signals to the external apparatus, the one or more biological signals being acquired by the acquisition section, and the external apparatus includes a reception unit that receives the one or more biological signals from the transmission unit, and a determination section that determines reliability of the one or more biological signals on the basis of reference data for a state of contact of the one or more electrode pairs with the skin, a body motion state of a user, and a state of pressure of the one or more electrode pairs on the skin, the one or more biological signals being received by the reception unit.

This application claims the priority on the basis of Japanese Patent Application No. 2017-199404 filed on Oct. 13, 2017 with Japan Patent Office, the entire contents of which are incorporated in this application by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. A biological information measurement device, comprising:

a plurality of electrode pairs configured to bring in contact with skin;

a control section configured to:

control a first connection and a first disconnection, between a first electrode of each electrode pair of the plurality of electrode pairs and a power supply section;

control a second connection and a second disconnection, between a second electrode of each of the electrode pair of the plurality of electrode pairs and a path leading to an Analog-to-Digital (AD) conversion section;

input a plurality of first analog signals to the AD conversion section, wherein each first analog signal of the plurality of first analog signals corresponds to a change in one of impedance or conductance between the first electrode and the second electrode of the respective electrode pair of the plurality of electrode pairs; and input a second analog signal to the AD conversion section, wherein the second analog signal corresponds to a change in one of impedance or conductance between a plurality of electrodes of the plurality of electrode pairs;

the AD conversion section configured to:

convert the plurality of first analog signals to a plurality of first digital signals; and convert the second analog signal to a second digital signal; and a processing section configured to derive a noise-reduced signal from the second digital signal, based on the plurality of first digital signals and the second digital signal, wherein a noise in the derived noise-reduced signal is less than the noise in the second digital signal.

2. The biological information measurement device according to claim 1, wherein the processing section is further configured to:

select at least one digital signal from the plurality of first digital signals, wherein the noise in the selected at least one digital signal is more than the noise in a set of first digital signals of the plurality of first digital signals; and subtract the selected at least one digital signal from the second digital signal to derive the noise-reduced signal.

3. The biological information measurement device according to claim 1, wherein in a case where the plurality of first digital signals includes a specific signal that saturates a measuring range of the AD conversion section, the processing section is further configured to derive the noise-reduced signal, based on at least one digital signal of the plurality of first digital signals excluding the specific signal and the second digital signal.

4. The biological information measurement device according to claim 1, further comprising
a connection and disconnection unit configured to execute the first connection and the first disconnection, and the second connection and the second disconnection, wherein
the processing section is further configured to control the first connection and the first disconnection, and the second connection and the second disconnection by the connection and disconnection unit, based on a plurality of control signals input to the connection and disconnection unit.

5. The biological information measurement device according to claim 1, further comprising:
a wiring board including the plurality of electrode pairs; and
a wrist fixation belt configured to support the wiring board to bring each electrode pair of the plurality of electrode pairs in contact with the skin of a wrist.

6. A biological information measurement system, comprising:
a wearable apparatus including:
a plurality of electrode pairs configured to bring in contact with skin;
a control section configured to:
control a first connection and a first disconnection, between a first electrode of each electrode pair of the plurality of electrode pairs and a power supply section;
control a second connection and a second disconnection, between a second electrode of each of the electrode pair of the plurality of electrode pairs and a path leading to an Analog-to-Digital (AD) conversion section;
input a plurality of first analog signals to the AD conversion section, wherein
each first analog signal of the plurality of first analog signals corresponds to a change in one of impedance or conductance between the first electrode and the second electrode of the respective electrode pair of the plurality of electrode pairs; and
input a second analog signal to the AD conversion section, wherein
the second analog signal corresponds to a change in one of impedance or conductance between a plurality of electrodes of the plurality of electrode pairs;
the AD conversion section configured to:
convert the plurality of first analog signals to a plurality of first digital signals; and
convert the second analog signal to a second digital signal;
a processing section configured to derive a noise-reduced signal from the second digital signal, based on the plurality of first digital signals and the second digital signal, wherein
a noise in the derived noise-reduced signal is less than the noise in the second digital signal; and
a transmission unit configured to transmit the noise-reduced signal to an external apparatus; and
the external apparatus including a reception unit configured to receive the noise-reduced signal from the transmission unit.

7. A biological information measurement system, comprising:
a wearable apparatus including:
a plurality of electrode pairs configured to bring in contact with skin;
a control section configured to:
control a first connection and a first disconnection; between a first electrode of each electrode pair of the plurality of electrode pairs and a power supply section;
control a second connection and a second disconnection, between a second electrode of each of the electrode pair of the plurality of electrode pairs and a path leading to an Analog-to-Digital (AD) conversion section;
input a plurality of first analog signals to the AD conversion section, wherein
each first analog signal of the plurality of first analog signals corresponds to a change in one of impedance or conductance between the first electrode and the second electrode of the respective electrode pair of the plurality of electrode pairs; and
input a second analog signal to the AD conversion section, wherein
the second analog signal corresponds to a change in one of impedance or conductance between a plurality of electrodes of the plurality of electrode pairs;
the AD conversion section configured to:
convert the plurality of first analog signals to a plurality of first digital signals; and
convert the second analog signal to a second digital signal; and
a transmission unit configured to transmit the plurality of first digital signals and the second digital signal to an external apparatus: and
the external apparatus including:
a reception unit configured to receive the plurality of first digital signals and the second digital signal from the transmission unit; and
a processing section configured to derive a noise-reduced signal from the second digital signal, based on the received plurality of first digital signals and the received second digital signal.

* * * * *